United States Patent [19]

Ferrini

[11] Patent Number: 5,380,726
[45] Date of Patent: Jan. 10, 1995

[54] SUBSTITUTED DIALKYLTHIO ETHERS

[75] Inventor: Pier G. Ferrini, Binningen, Switzerland

[73] Assignee: Ciba-Geigy Corporation, Ardsley, N.Y.

[21] Appl. No.: 170,110

[22] Filed: Dec. 20, 1993

[30] Foreign Application Priority Data

Jan. 15, 1993 [CH] Switzerland .................. 115/93-1

[51] Int. Cl.$^6$ ................ A61K 31/495; C07D 295/192; C07D 295/185
[52] U.S. Cl. .................... 514/255; 514/252; 514/253; 544/370; 544/372; 544/373; 544/391
[58] Field of Search ............. 544/391, 370, 372, 373; 514/255, 252, 253

[56] References Cited

U.S. PATENT DOCUMENTS

| | | | |
|---|---|---|---|
| 3,926,961 | 12/1975 | Ferrini et al. | 544/391 |
| 4,505,913 | 3/1985 | Ferrini et al. | 514/183 |
| 4,804,661 | 2/1989 | Ferrini et al. | 514/255 |
| 5,011,928 | 4/1991 | Venero | 544/373 |
| 5,286,728 | 2/1994 | Ferrini | 514/255 |
| 5,321,027 | 6/1994 | Ferrini et al. | 514/255 |

FOREIGN PATENT DOCUMENTS

| | | |
|---|---|---|
| 250361 | 12/1987 | European Pat. Off. . |
| 0385043 | 9/1990 | European Pat. Off. . |
| 0489690 | 6/1992 | European Pat. Off. . |
| 0524146 | 1/1993 | European Pat. Off. . |
| 2365988 | 3/1977 | Germany . |
| 874096 | 8/1961 | United Kingdom . |
| 2220206 | 1/1990 | United Kingdom . |
| 9000548 | 1/1990 | WIPO . |

OTHER PUBLICATIONS

J. Med Chem 26 (1983) pp. 1065–1070; Metz, et al. "Cloxacepride and Related Compounds . . . ".

J. Med. Chem. 33 (1990) 2883–91; Lis et al, "Synthesis of (Aryloxy)propanolamines and Related Compounds . . .".

Chem Abstr. 100, 174, 780c (1984) Agarwal et al.
Chem. Abstr. 112, 235261f (1990), Botros et al.
Chem. Abstr 87 52957h (1977), Liebenow et al.
Chem. Abstr. 56, 10165c (1962), Jacob et al.
Derwent Abstr. 87-357055/51 corresponding to EP.250,361 (1986).
Chem Abstr. 57, 15126h (1962), Jacob et al.
Chem Abstr. 58, 3444e (1963), Jacob et al.
Chem. Abstr. 58, 4583f (1963), Rhone-Poulec.
Chem Abstr. 58, 10211 (1963), Jacob et al.

*Primary Examiner*—Emily Bernhardt
*Attorney, Agent, or Firm*—Irving M. Fishman; Karen G. Kaiser

[57] ABSTRACT

Substituted dialkylthio ethers of formula I

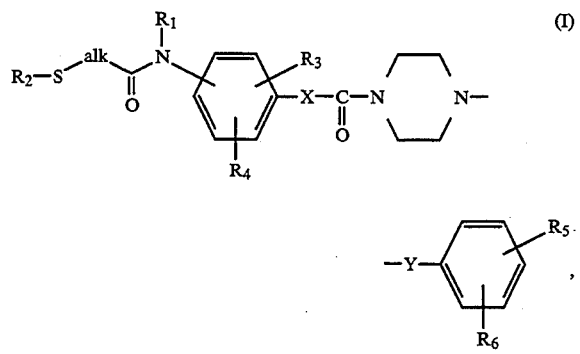

wherein $R_1$–$R_6$, alk, X and Y are as defined in the description, and salts thereof, exhibit properties inhibiting the biosynthesis of interleukin-1 (IL-1) and analgesic properties and can therefore be used as active ingredients in medicaments. They are prepared in a manner known per se.

12 Claims, No Drawings

SUBSTITUTED DIALKYLTHIO ETHERS

The invention relates to novel substituted dialkylthio ethers of formula I

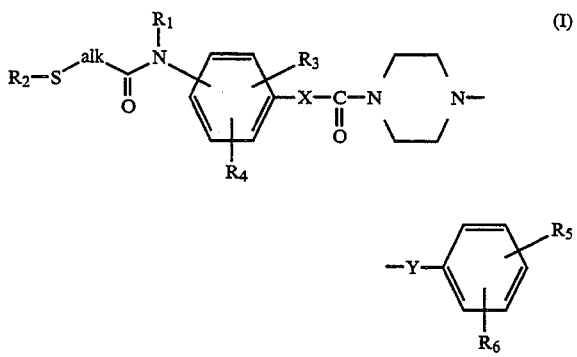

wherein
- $R_1$ is hydrogen, lower alkyl, hydroxy-lower alkyl, lower alkoxy-lower alkyl, lower alkoxy-lower alkoxy-lower alkyl, aryloxy-lower alkyl, aryl-lower alkoxy-lower alkyl, N-lower alkylamino-lower alkyl or N,N-di-lower alkylamino-lower alkyl;
- $R_2$ is lower alkyl that is substituted by a substituent selected from the group consisting of amino, acylamino, carboxy and functionally modified carboxy and that may carry further substituents selected from the group consisting of amino, lower alkylamino, di-lower alkylamino, acylamino, oxo, carboxy, functionally modified carboxy, hydroxy, lower alkoxy, acyloxy and halogen;
- $R_3$ and $R_4$ are each independently of the other hydrogen, lower alkyl, halogen, lower alkoxy or lower alkylthio;
- $R_5$ and $R_6$ are each independently or the other hydrogen, lower alkyl, halo-lower alkyl, lower alkoxy, lower alkylthio, halogen, amino, lower alkylamino, di-lower alkylamino or lower alkanoylamino;
- alk is lower alkylene; and
- X and Y are each independently of the other a direct bond, lower alkylene or lower alkenylene;

and salts thereof, to processes for the preparation of those compounds, to pharmaceutical compositions comprising those compounds, and to the use of those compounds in the therapeutic treatment of the human or animal body or in the preparation of pharmaceutical compositions.

Any compound of formula I that contains an asymmetric carbon atom can be in the form of a racemate or in the form of an R- or S-enantiomer. The invention relates to all those forms and, for example, also to diastereoisomers and mixtures thereof which may occur when two or more asymmetric centres are present in the molecule.

Hereinabove and hereinbelow "lower" radicals and compounds are to be understood as being, for example, those having up to and including 7, preferably up to and including 4, carbon atoms (C atoms).

Lower alkyl is, for example, $C_1$–$C_7$alkyl, preferably $C_1$–$C_4$alkyl, such as especially methyl or secondly ethyl, n-propyl, isopropyl or n-butyl, but may also be, for example, isobutyl, sec-butyl, tert-butyl or a pentyl, hexyl or heptyl group.

Halo-lower alkyl is, for example, trifluoromethyl.

Halogen is, for example, chlorine, fluorine or bromine, but may also be iodine.

Hydroxy-lower alkyl and lower alkoxy-lower alkyl carry the hydroxy or lower alkoxy group, respectively, preferably in a position higher than the α-position and are, for example, corresponding hydroxy-$C_2$–$C_4$alkyl or $C_1$–$C_4$alkoxy-$C_2$–$C_4$alkyl, for example 2-hydroxyethyl, 2-methoxyethyl, 2-ethoxyethyl, 2-propoxyethyl, 2-isopropoxyethyl, 3-methoxypropyl, 3-ethoxypropyl, 3-isopropoxypropyl or 4-methoxybutyl.

Oxo is the divalent substituent =O.

Carbamoyl is the group —C(=O)—$NH_2$.

Lower alkylene is, for example, methylene, ethylene, propylene, butylene or pentylene, but may also be, for example, hexylene or heptylene; it also includes branched radicals, for example 1-methyl-methylene, 1,1-dimethyl-methylene or 2-methyl-1,3-propylene. Lower alkylene as a definition of alk in formula I (or of $alk_1$ in formula Ia) is preferably $C_1$–$C_4$alkylene, especially methylene or 1,2-ethylene, but more especially methylene.

Lower alkylene as a definition of $alk_2$ in formula Ia, which may be unsubstituted or substituted, is preferably unsubstituted or substituted $C_1$–$C_4$alkylene and especially methylene. 1-methyl-methylene, 1,1-dimethyl-methylene, 1-(carboxy or functionally modified carboxy)-methylene or 1,2-ethylene.

Lower alkenylene is preferably $C_2$–$C_7$alkenylene, for example 1,3-propenylene, 1,4-butenylene and especially 1,2-ethenylene.

Aryl is, for example, phenyl that is unsubstituted or is substituted by one or two substituents from the group consisting of lower alkyl, lower alkoxy, hydroxy, halogen and trifluoromethyl, and is especially phenyl.

Acylamino is, for example, lower alkanoylamino or a radical —NH—$W_1$ wherein $W_1$ is the residue of an amino acid bonded via any carboxy group, or a derivative thereof. Acylamino is preferably lower alkanoylamino.

Acyloxy is, for example, lower alkanoyloxy.

Functionally modified carboxy is preferably lower alkoxycarbonyl, carbamoyl, N-lower alkylcarbamoyl, N,N-di-lower alkylcarbamoyl or cyano, but may also be, for example, a radical —C(=O)—$W_2$ wherein $W_2$ is the residue of an amino acid bonded via an amino group, or a derivative thereof.

An amino acid is to be understood as being, for example, an α- or β-amino acid, especially a natural α-amino acid having the L-configuration, such as normally occur in proteins, or an epimer of such an amino acid, that is to say having the unnatural D-configuration, or the corresponding D,L-isomeric mixture, or a homologue of such an amino acid, for example wherein the amino acid side chain has been lengthened or shortened by one or two methylene groups, wherein the amino group is in the β-position and/or wherein a methyl group has been replaced by hydrogen, or a substituted aromatic amino acid wherein the aromatic radical has from 6 to 14 carbon atoms, for example a substituted phenylalanine or phenylglycine wherein the phenyl ring is mono- or poly-substituted, for example, by lower alkyl, lower alkoxy, lower alkanoyloxy, amino, lower alkylamino, di-lower alkylamino, lower alkanoylamino, lower alkoxycarbonylamino, by arylmethoxycarbonylamino wherein aryl preferably has from 6 to 14 carbon atoms, for example benzyloxycarbonylamino or 9-fluorenylmethoxycarbonylamino, by halogen, carboxy and/or by nitro.

Derivatives of those amino acids are meant below, for example, when free amino or hydroxy functions, preferably a free amino function, are substituted by acyl radicals as defined above, and also when in those amino acids one or more carboxy groups are present in the form of functionally modified carboxy as defined above.

Salts of compounds of formula I are especially pharmaceutically acceptable salts, for example (a) acid addition salts with suitable mineral acids, such as hydrohalic acids, sulfuric acid or phosphoric acid, for example hydrochlorides, hydrobromides, sulfates, hydrogen sulfates or phosphates, salts with suitable aliphatic or aromatic sulfonic acids or N-substituted sulfamic acids, for example methanesulfonates, benzenesulfonates, p-toluenesulfonates or N-cyclohexylsulfamates (cyclamates), or salts with strong organic carboxylic acids, such as lower alkanecarboxylic acids or saturated or unsaturated or hydroxylated aliphatic dicarboxylic acids, for example acetates, oxalates, malonates, maleinates, fumarates, maleates, tartrates or citronates.

There are also included, for example, (b) corresponding salts with bases, such as corresponding alkali metal or alkaline earth metal salts, for example sodium, potassium or magnesium salts, pharmaceutically acceptable transition metal salts, such as zinc or copper salts, or salts with ammonia or organic amines, such as cyclic amines, such as mono-, di- or m-lower alkylamines, such as hydroxy-lower alkylamines, for example mono-, di- or tri-hydroxy-lower alkylamines, hydroxy-lower alkyl-lower alkylamines or polyhydroxy-lower alkylamines. Cyclic amines are, for example, morpholine, thiomorpholine, piperidine or pyrrolidine. There come into consideration as mono-lower alkylamines, for example, ethylamine and tert-butylamine; as di-lower alkylamines, for example, diethylamine and diisopropylamine; and as tri-lower alkylamines, for example, trimethylamine and triethylamine. Corresponding hydroxy-lower alkylamines are, for example, mono-, di- and tri-ethanolamine; hydroxy-lower alkyl-lower alkylamines are, for example, N,N-dimethylamino- and N,N-diethylamino-ethanol.

For the purposes of isolation or purification it is also possible to use pharmaceutically unacceptable salts. Only the pharmaceutically acceptable, non-toxic salts are used therapeutically and these are therefore preferred.

The compounds of formula I and the pharmaceutically acceptable salts thereof exhibit valuable pharmacological properties. They exhibit, especially, marked inhibitory action on the biosynthesis of interleukin-1 (IL-1). IL-1 belongs to the class of proinflammatory proteins and plays an essential role, for example, in the synthesis of prostaglandins, in the synthesis of neutral proteases by fibroblasts, synovial cells and chondrocytes, in the activation of endothelial cells and in the induction of other proinflammatory cytokines, such as the α-tumour necrosis factor (TNF) and interleukin-6 (IL-6). It also stimulates bone resorption, regulates the body temperature of warm-blooded animals and regulates inter alia the development, activation, differentiation and proliferation of lymphocytes. From the therapeutic standpoint, special importance is attached to the inhibitory action of compounds of formula I and the pharmaceutically acceptable salts thereof on the biosynthesis of IL-1, TNF and IL-6. This can be demonstrated in vitro, for example, using lipopolysaccharide-stimulated (LPS-stimulated) human monocytes in accordance with C. Rordorf-Adam et al., Drugs Exptl. Clin. Res. XV, 355–362 (1989) in a concentration range from approximately 0.1 $\mu$M and in vivo in mice by reference to the inhibition of the LPS-induced formation of serum amyloid P (SAP) at an $ED_{50}$ of approximately from 1 to 15 mg/kg p.o. and in rats by reference to the lowering of LPS-induced artificial fever at an $ED_{50}$ of approximately from 0.05 to 3.5 mg/kg p.o.

As a result of those properties, the compounds of formula I and the pharmaceutically acceptable salts thereof are excellently suitable for the therapeutic treatment of diseases in which an overproduction of IL-1 plays a causative or aggravating role, such as inflammatory and degenerative diseases of the joints, for example rheumatoid arthritis, osteo-arthrosis, psoriatic or infectious arthritis, Reiter's syndrome, gout and traumatic arthritis, and other acute or chronic inflammations, for example inflammatory intestinal diseases, meningitis, skin diseases, for example psoriasis or Pemphigus vulgaris, allergic skin reactions, atherosclerosis and autoimmune diseases, such as diabetes (type 1) and thyroiditis.

Examples of other diseases in which an overproduction of IL-1 plays a causative or aggravating role are, for example: bone metabolism regulation disorders, for example Paget's disease, osteoporosis, periodontitis or malignancies; or endotoxic shock, for example associated with fever, hypotension and fulminant liver failure.

The compounds of formula I and the pharmaceutically acceptable salts thereof also have a marked analgesic action which can be demonstrated, tier example, by reference to the inhibition of the phenyl-p-benzoquinone-induced writhing syndrome in mice, for example in an experimental procedure based on Hendershot and Forsaith, J. Pharmacol. Exp. Therap. 125,237 (1959), at an $ED_{50}$ or approximately from 1 to 30 mg/kg p.o.

Accordingly, the compounds of formula I and the pharmaceutically acceptable salts thereof can also be used as active ingredients in analgesic medicaments for the treatment of painful conditions of different origins, especially as peripheral analgesics.

The invention relates preferably to compounds of formula I wherein $R_1$ is hydrogen, lower alkyl, hydroxy-lower alkyl, lower alkoxy-lower alkyl, lower alkoxy-lower alkoxy-lower alkyl; phenoxy-lower alkyl or phenyl-lower alkoxy-lower alkyl, the phenyl group in each of the two last-mentioned radicals being unsubstituted or substituted by lower alkyl, trifluoromethyl, lower alkoxy, halogen and/or by hydroxy; N-lower alkylamino-lower alkyl or N,N-di-lower alkylamino-lower alkyl;

$R_2$ is lower alkyl that is substituted by a substituent selected from the group consisting of amino, lower alkanoylamino, carboxy, lower alkoxycarbonyl, carbamoyl, N-lower alkylcarbamoyl, N,N-di-lower alkylcarbamoyl, cyano and a radical —C(=O)—$W_2$ wherein $W_2$ is the residue of an amino acid bonded via an amino group, or a derivative thereof, and that may carry further substituents selected from the group consisting of amino, lower alkylamino, di-lower alkylamino, lower alkanoylamino, a radical —NH—$W_1$ wherein $W_1$ is the residue of an amino acid bonded via any carboxy group, or a derivative thereof; and oxo, carboxy, lower alkoxycarbonyl, carbamoyl, N-lower alkylcarbamoyl, N,N-di-lower alkylcarbamoyl, cyano, hydroxy, lower alkoxy, lower alkanoyloxy and halogen;

$R_3$ and $R_4$ are each independently of the other hydrogen, lower alkyl, halogen, lower alkoxy or lower alkylthio;

$R_5$ and $R_6$ are each independently of the other hydrogen, lower alkyl, halo-lower alkyl, lower alkoxy, lower alkylthio, halogen, amino, lower alkylamino, di-lower alkylamino or lower alkanoylamino;

alk is lower alkylene; and

X and Y are each independently of the other a direct bond, lower alkylene or lower alkenylene;

and salts thereof.

The invention relates especially to compounds of formula I wherein $R_1$ is hydrogen, lower alkyl, hydroxy-lower alkyl, lower alkoxy-lower alkyl, lower alkoxy-lower alkoxy-lower alkyl, phenoxy-lower alkyl, N-lower alkylamino-lower alkyl or N,N-di-lower alkylamino-lower alkyl;

$R_2$ is lower alkyl that is substituted by a substituent selected from the group consisting of amino, carboxy, lower alkoxycarbonyl, carbamoyl, N-lower alkylcarbamoyl, N,N-di-lower alkylcarbamoyl and a radical —C(=O)—$W_2$ wherein $W_2$ is the residue, bonded via an amino group, of a natural amino acid selected from glycine, alanine, valine, leucine and serine, or a lower alkyl ester thereof, and that may carry a further substituent selected from the group consisting of amino, lower alkanoylamino, a radical —NH—$W_1$ wherein $W_1$ is the residue, bonded via any carboxy group, of a natural amino acid selected from glutamic acid, aspartic acid, glycine, alanine, valine, leucine and serine, or a lower alkyl ester thereof; and oxo, carboxy, lower alkoxycarbonyl, carbamoyl, N,N-di-lower alkylcarbamoyl and hydroxy;

$R_3$ and $R_4$ are each independently of the other hydrogen, lower alkyl, halogen, lower alkoxy or lower alkylthio;

$R_5$ and $R_6$ are each independently of the other hydrogen, lower alkyl, trifluoromethyl, lower alkoxy, lower alkylthio, halogen or di-lower alkylamino;

alk is lower alkylene; and

X and Y are each independently or the other a direct bond, lower alkylene or lower alkenylene;

and salts thereof.

The invention relates more especially to compounds of formula I wherein $R_1$ is hydrogen, lower alkyl, hydroxy-lower alkyl or lower alkoxy-lower alkyl;

$R_2$ is lower alkyl that is substituted by a substituent selected from the group consisting of amino, carboxy, lower alkoxycarbonyl and a radical —C(=O)—$W_2$ wherein $W_2$ is the residue, bonded via the amino group, of the amino acid glycine, or a lower alkyl ester thereof, and that may carry a further substituent selected from the group consisting of amino, lower alkanoylamino, a radical —NH—$W_1$ wherein $W_1$ is the residue, bonded via the γ-carboxy group, of the amino acid L-glutamic acid, or a lower alkyl ester thereof; and oxo, carboxy and lower alkoxycarbonyl;

$R_3$ and $R_4$ are each independently of the other hydrogen, lower alkyl, halogen, lower alkoxy or lower alkylthio;

$R_5$ is lower alkylthio, chlorine, fluorine or bromine;

$R_6$ is hydrogen;

alk is methylene;

X is a direct bond or 1,2-ethenylene; and

Y is 1,2-ethylene;

and pharmaceutically acceptable salts thereof.

Of the compounds of formula I special mention should be made of compounds of formula Ia

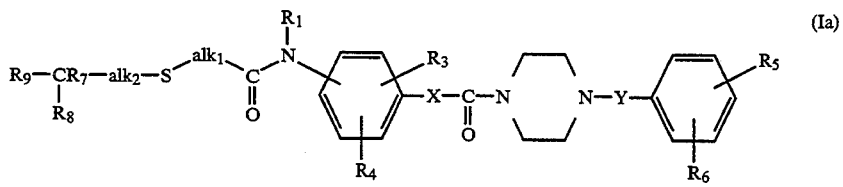

wherein $R_1$ is hydrogen, lower alkyl, hydroxy-lower alkyl or lower alkoxy-lower alkyl;

$R_3$ and $R_4$ are each independently of the other hydrogen, lower alkyl, chlorine, fluorine, bromine, lower alkoxy or lower alkylthio;

$R_5$ and $R_6$ are each independently of the other chlorine, fluorine, bromine, hydrogen, lower alkyl, trifluoromethyl, lower alkoxy or lower alkylthio;

$R_7$ is hydrogen;

$R_8$ is hydrogen, amino, lower alkanoylamino or a radical —NH—$W_1$ wherein $W_1$ is the residue, bonded via any carboxy group, of an amino acid, or a derivative thereof; or $R_7$ and $R_8$ together are oxo;

$R_9$ is amino, lower alkanoylamino, carboxy, lower alkoxycarbonyl, carbamoyl, N-lower alkylcarbamoyl, N,N-di-lower alkylcarbamoyl, cyano or a radical —C(=O)—$W_2$ wherein $W_2$ is the residue, bonded via an amino group, of an amino acid, or a derivative thereof;

$alk_1$ is lower alkylene;

$alk_2$ is a direct bond or lower alkylene that is unsubstituted or substituted by carboxy, lower alkoxycarbonyl, carbamoyl, N-lower alkylcarbamoyl, N,N-di-lower alkylcarbamoyl or by cyano;

X is a direct bond or 1,2-ethenylene; and

Y is a direct bond, lower alkylene or 1,2-ethenylene;

and salts thereof.

The invention relates especially to compounds of formula Ia wherein $R_1$ is hydrogen, lower alkyl, hydroxy-lower alkyl or lower alkoxy-lower alkyl;

$R_3$ and $R_4$ are each independently of the other hydrogen, lower alkyl, chlorine, fluorine or bromine;

$R_5$ is chlorine, fluorine, bromine or lower alkylthio;

$R_6$ is hydrogen;

$R_7$ is hydrogen;

$R_8$ is hydrogen, amino, lower alkanoylamino or a radical —NH—$W_1$ wherein $W_1$ is the residue, bonded via any carboxy group, of a natural amino acid, or a lower alkyl ester thereof; or $R_7$ and $R_8$ together are oxo;

$R_9$ is amino, carboxy, lower alkoxycarbonyl, carbamoyl, N-lower alkylcarbamoyl, N,N-di-lower alkylcarbamoyl or a radical —C(═O)—W$_2$ wherein W$_2$ is the residue, bonded via an amino group, of a natural amino acid, or a lower alkyl ester thereof;

alk$_1$ is methylene;

alk$_2$ is a direct bond, methylene, 1-methyl-methylene, 1,1-dimethyl-methylene, 1-(carboxy or lower alkoxycarbonyl)-methylene or 1,2-ethylene;

X is a direct bond or 1,2-ethenylene; and

Y is 1,2-ethylene;

and pharmaceutically acceptable salts thereof.

The invention relates more especially to compounds of formula Ia wherein

R$_1$ is hydrogen, C$_1$-C$_4$alkyl, hydroxy-C$_2$-C$_4$alkyl or C$_1$-C$_4$alkoxy-C$_2$-C$_4$alkyl;

R$_3$ and R$_4$ are each independently of the other hydrogen, lower alkyl, chlorine, fluorine or bromine;

R$_5$ is linked in the para-position and is chlorine, fluorine, bromine or lower alkylthio;

R$_6$ is hydrogen;

R$_7$ is hydrogen;

R$_8$ is hydrogen, amino, lower alkanoylamino or a radical —NH—W$_1$ wherein W$_1$ is the residue, bonded via any carboxy group, of a natural amino acid selected from glutamic acid, aspartic acid, glycine, alanine, valine, leucine and serine, or a lower alkyl ester thereof; or R$_7$ and R$_8$ together are oxo;

R$_9$ is amino, carboxy, lower alkoxycarbonyl, carbamoyl, N-lower alkylcarbamoyl, N,N-di-lower alkylcarbamoyl or a radical —C(═O)—W$_2$ wherein W$_2$ is the residue, bonded via an amino group, of a natural amino acid selected from glycine, alanine, valine, leucine and serine, or a lower alkyl ester thereof;

alk$_1$ is methylene;

alk$_2$ is a direct bond, methylene, 1,1-dimethyl-methylene, 1-(carboxy or lower alkoxycarbonyl)methylene or 1,2-ethylene;

X is a direct bond or 1,2-ethenylene; and

Y is 1,2-ethylene;

and pharmaceutically acceptable salts thereof.

The invention relates especially to compounds of formula Ia wherein

R$_1$ is hydrogen, methyl, ethyl, 2-hydroxyethyl or 2-isopropoxyethyl;

R$_3$ and R$_4$ are each independently of the other hydrogen, methyl, chlorine or fluorine;

R$_5$ is linked in the para-position and is chlorine or bromine;

R$_6$ is hydrogen;

R$_7$ is hydrogen;

R$_8$ is hydrogen, amino, lower alkanoylamino or a radical —NH—W$_1$ wherein W$_1$ is the residue, bonded via the γ-carboxy group, of the amino acid L-glutamic acid, or a lower alkyl ester thereof; or R$_7$ and R$_8$ together are oxo;

R$_9$ is amino, carboxy, lower alkoxycarbonyl or a radical —C(═O)—W$_2$ wherein W$_2$ is the residue, bonded via the amino group, of the amino acid glycine, or a lower alkyl ester thereof;

alk$_1$ is methylene;

alk$_2$ is a direct bond, methylene, 1,1-dimethyl-methylene, 1-(carboxy or lower alkoxycarbonyl)methylene or 1,2-ethylene;

X is a direct bond or 1,2-ethenylene; and

Y is 1,2-ethylene;

and pharmaceutically acceptable salts thereof.

When, in a compound of formula Ia, R$_9$ is amino or lower alkanoylamino, the radical R$_8$ is preferably hydrogen. When, in a compound of formula Ia, alk$_2$ is a direct bond, the radical R$_8$ is preferably hydrogen.

In all the different groups of compounds of formula Ia that are mentioned above, further emphasis is given to those compounds of formula Ia wherein R$_8$ is lower alkanoylamino.

The invention relates specifically to the compounds of formula I mentioned in the Examples and salts thereof, especially pharmaceutically acceptable salts thereof.

The process for the preparation of compounds of formula I, which include all the compounds of formula Ia, is based on methods known per se and is carried out, for example, as follows:

a) a compound of formula II

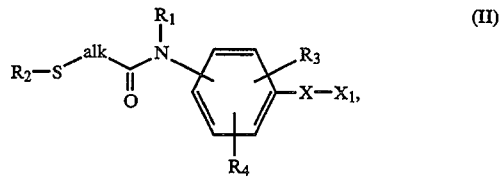

wherein X$_1$ is carboxy or reactive functionally modified carboxy, or a salt thereof, is reacted with a compound of formula III

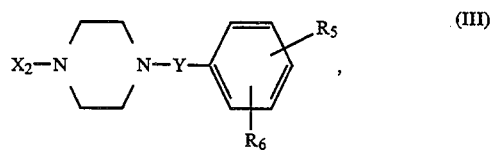

wherein X$_2$ is hydrogen or an amino-protecting group, or b) a compound of formula IV

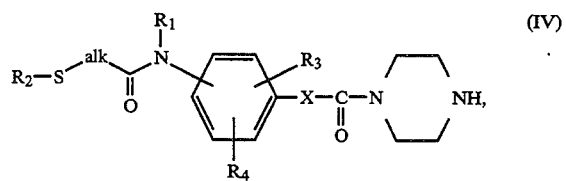

or a salt thereof, is reacted with a compound of formula V

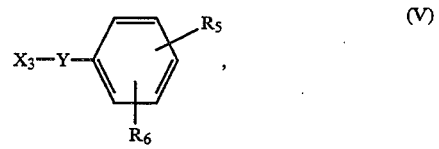

wherein X$_3$ is hydroxy or reactive esterified hydroxy, or c) a compound of formula VI

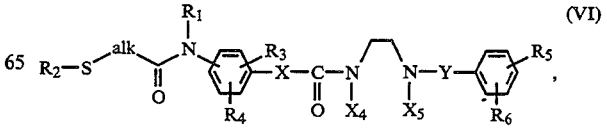

wherein one of the radicals $X_4$ and $X_5$ is hydrogen and the other is a group of the formula —$CH_2$—$CH_2$—$X_3$ (VIa) and $X_3$ is hydroxy or reactive esterified hydroxy, is cyclised, or d) a compound of formula VII

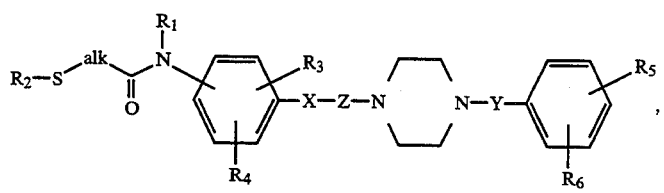

(VII)

wherein Z is a group that can be oxidised to carbonyl, is oxidised, or e) a compound of formula VIII

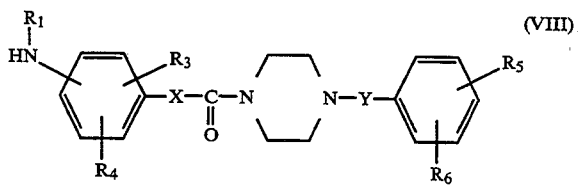

(VIII)

is acylated by reaction with a compound of formula IX

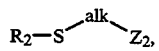

wherein $Z_2$ is carboxy or a reactive carboxy derivative, or f) a compound of formula X

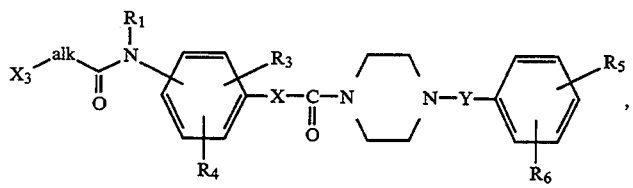

wherein $X_3$ is hydroxy or reactive esterified hydroxy, is reacted with a compound of the formula $R_2$—SH;

and, if desired, a compound of formula I obtainable in accordance with any one of the above processes or by another method is converted into a different compound of formula I, a mixture of isomers obtainable in accordance with the process is separated into its components, a tree compound of formula I obtainable in accordance with the process is converted into a salt and/or a salt obtainable in accordance with the process is converted into the free compound of formula I or into a different salt.

The reactions described hereinabove and hereinbelow are carried out in a manner known per se, for example in the absence or, usually, in the presence of a suitable solvent or diluent or a mixture thereof, the operation being carried out, as required, with cooling, at room temperature or with heating, for example in a temperature range of from approximately —78° to the boiling temperature of the reaction medium, preferably from approximately —10° to approximately 150° C., and, if necessary, in a closed vessel, under pressure, in an inert gas atmosphere and/or under anhydrous conditions.

In the starting materials the basic centre can be, for example, in the form of an acid addition salt, for example with an acid listed above in connection with salts of compounds of formula I, while starting compounds of formula II wherein $X_1$ is carboxy can form salts with bases. Suitable salts with bases are, for example, corresponding alkali metal or alkaline earth metal salts, for example sodium, potassium or magnesium salts, pharmaceutically acceptable transition metal salts, such as zinc or copper salts, or salts with ammonia or organic amines, such as cyclic amines, such as mono-, di- or tri-hydroxy-$C_1$-$C_7$alkylamines, hydroxy-$C_1$-$C_7$alkyl-$C_1$-$C_7$alkylamines or polyhydroxy-$C_4$-$C_7$alkylamines. Cyclic amines are, for example, morpholine, thiomorpholine, piperidine or pyrrolidine. There come into consideration as mono-$C_1$-$C_7$alkylamines, for example, ethylamine or tert-butylamine; as di-$C_1$-$C_7$alkylamines, for example, diethylamine or di-isopropylamine; and as tri-$C_1$-$C_7$alkylamines, for example, trimethylamine or triethylamine. Corresponding hydroxy-$C_1$-$C_7$alkylamines are, for example, mono-, di- or triethanolamines, and hydroxy-$C_1$-$C_7$alkyl-$C_1$-$C_7$alkylamines are, for example, N,N-dimethylamino- or N,N-diethylaminoethanol, and also glucosamine as a polyhydroxy-$C_6$alkylamine.

Reactive functionally modified carboxy $X_1$ is, for example, esterified carboxy, especially reactive esterified carboxy, anhydridised carboxy or amidated carboxy.

Esterified carboxy is, for example, unsubstituted or substituted $C_1$-$C_7$alkoxycarbonyl, such as ethoxycarbonyl, but preferably reactive esterified carboxy, for example vinyloxycarbonyl, which may be additionally activated, for example, by $C_1$-$C_7$alkoxy or by unsubstituted or substituted carbamoyl, such as 1-$C_1$-$C_7$alkoxy-, for example 1-ethoxyvinyloxycarbonyl, or 2-(N-$C_1$-$C_7$alkylcarbamoyl)-, for example 2-(N-ethylcarbamoyl)-vinyloxycarbonyl, and also phenoxy- or thiophenoxycarbonyl that is unsubstituted or substituted, for example, by nitro, halogen, $C_1$-$C_7$alkanesulfonyl or by phenylazo, such as 4-nitro-, 2,4,5-trichloro-, pentachloro-, 4-methanesulfonyl-, 4-phenylazo-phenoxycarbonyl, thiophenoxy- or 4-nitrothiophenoxy-carbonyl, and also activated methoxycarbonyl, for example methoxycarbonyl substituted by cyano or by free or esterified carboxy, especially cyanomethoxycarbonyl. Reactive esterified carboxy can also be 1,1- or 1,3-disubstituted 2-isoureidocarbonyl, such as 1,1-di-lower alkyl- , 1,1-diaryl- or 1,1-diaryl-$C_1$-$C_7$ alkyl-2-isoureidocarbonyl, for example 1,1-diethyl-, 1,1-diphenyl- or 1,1-dibenzyl-2-isoureidocarbonyl, or 1,3-dicycloalkyl-, for example 1,3-dicyclohexyl-2-isoureidocarbonyl, or N-$C_2$-$C_7$alkyleneamino-oxycarbonyl, such as N-piperidinyl-oxycarbonyl, and also N-imido-oxycarbonyl, for example N-succinimido-oxy- or N-phthalimido-oxycarbonyl.

Anhydridised carboxy is to be understood as being, for example, unbranched or branched $C_1$-$C_7$alkoxycarbonyloxycarbonyl, such as ethoxy- or isobutoxy-carbonyloxycarbonyl, halocarbonyl, such as chlorocarbonyl, azidocarbonyl, halophosphoryloxycarbonyl, such as dichlorophosphoryloxycarbonyl, or unsubstituted or substituted, for example halo- or aryl-substituted, $C_1$-$C_7$alkanoyloxycarbonyl, such as pivaloyloxy-, trifluoroacetoxy- or phenylacetoxy-carbonyl.

Reactive amidated carboxy is, for example, unsubstituted or substituted, for example $C_1$-$C_7$alkyl-substituted, 1-imidazolyl- or 1-pyrazolyl-carbonyl, such as 3,5-dimethylpyrazolylcarbonyl.

An amino-protecting group $X_2$ is, for example, acyl, such as $C_1$-$C_7$alkanoyl, for example formyl or acetyl, halocarbonyl, such as chlorocarbonyl, and also unsubstituted or substituted aryl- or heteroaryl-sulfonyl, such as 2-pyridyl- or 2-nitrophenyl-sulfonyl.

In the context of the description of the process hereinabove and hereinbelow, unless otherwise defined, reactive esterified hydroxy, for example $X_3$, is especially hydroxy esterified by a strong inorganic acid or organic sulfonic acid, for example halogen, such as chlorine, bromine or iodine, sulfonyloxy, such as hydroxysulfonyloxy, halosulfonyloxy, for example fluorosulfonyloxy, unsubstituted or substituted, for example halo-substituted, $C_1$-$C_7$alkanesulfonyloxy, for example methane- or trifluoromethane-sulfonyloxy, $C_3$-$C_7$cycloalkanesulfonyloxy, for example cyclohexanesulfonyloxy, or unsubstituted or substituted, for example $C_1$-$C_7$alkyl- or halo-substituted, benzenesulfonyloxy, for example p-bromophenyl- or p-toluene-sulfonyloxy.

Where, for example, bases are used in the reactions described hereinabove and hereinbelow, unless specified to the contrary, the following come into consideration, for example: alkali metal hydroxides, hydrides, amides, alkanolates, carbonates, triphenylmethylides, di-$C_1$-$C_7$alkylamides, amino-$C_1$-$C_7$alkylamides or $C_1$-$C_7$alkylsilylamides, or naphthylamines, $C_1$-$C_7$alkylamines, basic heterocycles, ammonium hydroxides, and also carbocyclic amines. There may be mentioned by way of example: lithium hydroxide, sodium hydroxide, hydride, amide or ethanolate, potassium tert-butanolate or carbonate, lithium triphenylmethylide or diisopropylamide, potassium 3-(aminopropyl)amide or bis-(trimethylsilyl)amide, dimethylaminonaphthalene, di- or tri-ethylamine, pyridine, benzyltrimethylammonium hydroxide, 1,5-diazabicyclo[4.3.0]non-5-ene (DBN) and also 1,8-diazabicyclo[5.4.0]undec-7-ene (DBU).

Variant a): The N-acylation in accordance with the process is carried out in a manner known per se, if necessary in the presence of a condensation agent, especially a basic condensation agent. Suitable bases are, for example, representatives of the bases listed above. Frequently the basicity of the compound of formula III is also sufficient.

When $X_1$ is carboxy there are formed, for example, primarily the corresponding ammonium salts which can be dehydrated by heating or by treatment with suitable dehydrating agents (as condensation agents), such as carbodiimides, for example N,N'-di-lower alkyl- or N,N'-dicycloalkyl-carbodiimide, such as N,N'-diethyl-, N,N'-diisopropyl- or N,N'-dicyclohexyl-carbodiimide, advantageously with the addition of N-hydroxysuccinimide or unsubstituted or substituted, for example halo-, lower alkoxy- or lower alkyl-substituted, 1-hydroxybenzotriazole or N-hydroxy-5-norbornene-2,3-dicarboxamide, and also N,N-carbonyldiimidazole. With carbodiimides it is possible to form intermediately, for example, also the corresponding 1-isoureidocarbonyl compounds. As water-binding condensation agents there may also be used N-ethoxycarbonyl-2-ethoxy-1,2-dihydroquinoline, phosphorylcyanamides or phosphorylazides, such as diethylphosphorylcyanamide or diphenylphosphorylazide, triphenylphosphine disulfide or 1-lower alkyl-2-halopiperidinium halides, such as 1-methyl-2-chloropyridinium iodide.

Some of the starting materials used in this process variant are known or they can be prepared according to processes known per se.

For the preparation of compounds of formula II wherein $X_1$ is unsubstituted or substituted $C_1$-$C_7$alkoxycarbonyl it is usually possible to use as starting material the free acid ($X_1$=carboxy) or an acid anhydride ($X_1$ is, for example, halocarbonyl), which is reacted, for example, with the corresponding alcohol, which is if necessary in reactive form, for example a $C_1$-$C_7$alkyl halide. The preparation of compounds of formula II wherein $X_1$ is vinyloxycarbonyl, which may be additionally activated, can be carried out, for example, by transesterification of a $C_1$-$C_7$alkyl ester with vinyl acetate (activated vinyl ester method), by reaction of the free acid of compounds of formula II with lower alkoxyacetylene (for example ethoxyacetylene method) or, analogously to the Woodward method, with a 1,2-oxazolium salt. Compounds of formula II containing unsubstituted or substituted phenoxy- or thiophenoxycarbonyl can be obtained, for example, starting from the free acid in accordance with the carbodiimide method by reaction with the corresponding (thio)phenol. Likewise starting from the free acid of formula II it is possible to obtain compounds of formula II wherein $X_1$ is activated methoxycarbonyl or 1,1- or 1,3-disubstituted 2-isoureidocarbonyl, for example by reaction with a haloacetonitrile, for example chloroacetonitrile, (cyanomethyl ester method) or with a carbodiimide or cyanamide (carbodiimide or cyanamide method), respectively. The preparation of N-$C_2$-$C_7$alkyleneaminooxycarbonyl or N-imido-oxycarbonyl compounds of formula II can be carded out, for example, using the free acid of formula II from corresponding N-hydroxy compounds with the aid of carbodiimides in accordance with the activated N-hydroxy esters method. For the preparation of compounds of formula II wherein $X_1$ is unbranched or branched $C_1$-$C_7$alkoxycarbonyloxycarbonyl, halophosphoryloxycarbonyl or unsubstituted or substituted $C_1$-$C_7$alkanoyloxycarbonyl, there can be used as starting material, for example, the free acid of formula II which can be treated, for example, with a corresponding halide, such as an unsubstituted or substituted $C_1$-$C_7$alkylcarbonic acid halide (mixed O-carbonic acid anhydrides method), phosphorus oxyhalide (for example phosphorus oxychloride method) or an unsubstituted or substituted $C_1$-$C_7$alkanoyl halide (mixed carboxylic acid halides method). Azidocarbonyl compounds of formula II can be obtained, for example, by treatment of corresponding hydrazides with nitrous acid (azide method). For the preparation of compounds of formula II wherein $X_1$ is unsubstituted or substituted 1-imidazolylcarbonyl or 1-pyrazolylcarbonyl, the free acid of formula II is reacted, for example, with di(1-imidazolyl)carbonyl (imidazolide method) or the relevant hydrazide, for example with a corresponding 1,3-diketone (pyrazolide method), respectively.

Variant b): The radical $X_3$ is especially reactive esterified hydroxy, for example halogen, such as chlorine.

The N-alkylation in accordance with the process is carried out in a manner known per se, if necessary in the presence of a base, for example one of the bases mentioned above.

Some of the starting materials used in this process variant are known or they can be prepared in a manner known per se.

For example, the staring material of formula IV can be prepared by reacting a compound of formula II, or a salt thereof, wherein $X_1$ is carboxy or reactive functionally modified carboxy with a compound of formula IVa

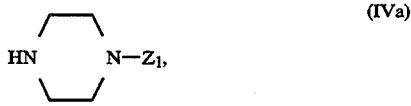

or a salt thereof, wherein $Z_1$ is hydrogen or an amino-protecting group, such as benzyl, in the manner described in variant a) and, where appropriate, removing the amino-protecting group, for example benzyl, by customary hydrogenolysis.

Variant c): The cyclisation (intramolecular N-alkylation) in accordance with the process is carried out in a manner known per se, if necessary in the presence of a condensation agent, especially a basic condensation agent. The bases used are, for example, those mentioned above.

$X_3$ is in this case especially reactive esterified hydroxy, preferably halogen, such as chlorine.

The starting material can be prepared in a manner known per se, for example starting from a compound of formula II, or a salt thereof, wherein $X_1$ is carboxy or reactive functionally modified carboxy, which compound is first reacted with a compound of formula

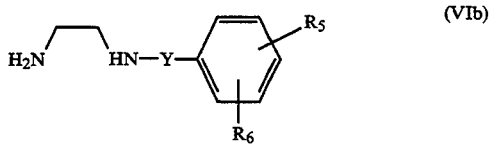

analogously to variant a). In the next reaction step the resulting compound is reacted with a compound of the formula $X_3$—$CH_2$—$CH_2$—$X_3$ (VIc) under N-alkylating conditions in accordance with variant b).

Variant d): A group Z that can be oxidised to —CO— is especially —$CH_2$—. The oxidation of corresponding compounds of formula VII is effected with the aid of a suitable oxidising agent, there preferably being used tetra-$C_1$-$C_4$alkylammonium permanganates that are unsubstituted or substituted, for example by a phenyl radical, especially benzyltriethylammonium permanganate.

The starting material of formula VII is prepared in a manner known per se, for example starting from a compound of formula III wherein $X_2$ is hydrogen, which compound is reacted under the N-alkylating conditions described in variant b) with a compound of formula VIIa

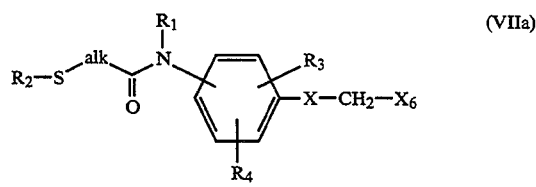

wherein $X_6$ is hydroxy or especially reactive esterified hydroxy, especially halogen, such as chlorine or bromine.

Variant e): A reactive carboxy derivative is, for example, an acid halide or anhydride, or one of the reactive esterified carboxy derivatives mentioned above.

The introduction of the acyl radical in accordance with variant e) (N-acylation) is carried out in customary manner [see also variant a)], if necessary in the presence of a condensation agent, especially a basic condensation agent. Suitable bases are, for example, representatives of the bases mentioned above.

Variant f): Variant f) relates to the S-alkylation, known per se, of mercaptans. In the reaction. If necessary, a base is added, for example aqueous ammonia solution or another of the bases mentioned above.

When, in the reaction according to f), the compound $R_2$—SH is, for example, L-glutathione or a derivative thereof, instead of a base it is also possible to add a corresponding enzyme, for example glutathione-S-transferase.

A compound according to the invention obtainable in accordance with the process or by another method can be converted into another compound according to the invention in a manner known per se, for example by reactions known per se, such as the hydrolysis of esters to carboxylic acids, the esterification of carboxylic acids, or the N-alkylation or N-acylation of amino groups.

Resulting salts can be converted into the tree compounds in a manner known per se, for example by treatment with a base, such as an alkali metal hydroxide, a metal carbonate or hydrogen carbonate, or ammonia, or with another salt-forming base mentioned at the beginning, or with an acid, such as a mineral acid, for example hydrochloric acid, or with another salt-forming acid mentioned at the beginning.

Resulting salts can be convened into different salts in a manner known per se: acid addition salts, for example, by treatment with a suitable metal salt, such as a sodium, barium or silver salt, of a different acid in a suitable solvent in which an inorganic salt being formed is insoluble and is therefore eliminated from the reaction equilibrium, and basic salts by freeing the free acid and converting it into a salt again.

The compounds of formula I, including their salts, may also be obtained in the form of hydrates or may include the solvent used for crystallisation.

As a result of the close relationship between the novel compounds in tree form and in the form of their salts, hereinabove and hereinbelow any reference to the tree compounds and their salts is to be understood as including also the corresponding salts and free compounds, respectively, as appropriate and expedient.

The invention relates also to those forms of the process according to which a compound obtainable as intermediate at any stage of the process is used as starting material and the remaining steps are carried out or a starting material is used in the form of a salt or especially is formed under the reaction conditions.

The invention relates also to the novel starting materials, which have been developed specifically for the preparation of the compounds according to the invention, especially the group of starting materials that result in the compounds of formula I described at the beginning as being preferred, to processes for the preparation thereof and to the use thereof as intermediates.

The novel compounds of formula I can be used, for example, in the form of pharmaceutical compositions comprising a therapeutically effective amount of the active ingredient, optionally together with inorganic or organic, solid or liquid, pharmaceutically acceptable carriers that are suitable for enteral, for example oral, or parenteral administration. For example, there are used tablets or gelatin capsules comprising the active ingredient together with diluents, for example lactose, dextrose, saccharose, mannitol, sorbitol, cellulose and/or lubricants, for example silica, talc, stearic acid or salts thereof, such as magnesium or calcium stearate, and/or polyethylene glycol. Tablets may also comprise binders, for example magnesium aluminium silicate, starches, such as corn, wheat, rice or arrowroot starch, gelatin, tragacanth, methylcellulose, sodium carboxymethylcellulose and/or polyvinylpyrrolidone, and, if desired, disintegrators, for example starches, agar, alginic acid or a salt thereof, for example sodium alginate, and/or effervescent mixtures, or absorbents, colourings, flavourings and sweeteners. The novel compounds of formula I can also be used, for example, in the form of parenterally administrable compositions or in the form of infusion solutions. Such solutions are preferably isotonic aqueous solutions or suspensions, it being possible, for example in the case of lyophilised compositions that comprise the active ingredient on its own or together with a carrier, for example mannitol, for such solutions or suspensions to be made up before use. The pharmaceutical compositions may be sterilised and/or comprise excipients, for example preservatives, stabilisers, wetting agents and/or emulsifiers, solubilisers, salts for regulating the osmotic pressure and/or buffers. The present pharmaceutical compositions which, if desired, may comprise further pharmacologically active ingredients, are prepared in a manner known per se, for example by means of conventional mixing, granulating, confectioning, dissolving or lyophilising processes, and comprise approximately from 0.1% to 100%, especially from approximately 1% to approximately 50%, and in the case of lyophilisates up to 100%, active ingredient.

The invention relates also to the use of the compounds of formula I, preferably in the form of pharmaceutical compositions. The dose may depend on various factors, such as mode of administration, species, age and/or individual condition. The daily doses to be administered in the case of oral administration are from approximately 0.25 to approximately 10 mg/kg and for warm-blooded animals of approximately 70 kg body weight preferably from approximately 20 mg to approximately 500 mg.

The following Examples serve to illustrate the invention; temperatures are given in degrees Celsius, pressures in mbar. The following abbreviations are used: ether=diethyl ether, (BOC)$_2$O=di-tert-butyl dicarbonate.

EXAMPLE 1

(—)-1-{4-[N-2-isopropoxyethyl)-N-([2R]-2-methoxycarbonyl-2-aminoethylmercapto-acetyl)-amino]-benzoyl}-4-[2-(4-chlorophenyl)-ethyl]-piperazine dihydrochloride trihydrate 2 g of 1-{4-[N-(2-isopropoxyethyl)-N-chloroacetylamino]-benzoyl}-4-[2-(4-chlorophenyl)-ethyl]-piperazine hydrochloride, m.p. 146°–147°, (see EP-A-524 146, Examples 3 and 2) are suspended in 50 ml of water. 3.16 g of L-cysteine methyl ester hydrochloride (supplied by Fluka) and then 20 ml of ether are added. 2 ml of concentrated aqueous ammonia solution are added, with stirring. An emulsion having a pH of about 10 is formed. Clear layers form within a short period of time. After being stirred vigorously for 2 hours, the two-phase reaction mixture is diluted with ether; the organic phase is separated off and washed with water, dried and concentrated by evaporation. Ethereal hydrochloric acid is added to the oily material followed by crystallisation from dichloromethane/ether. The title compound having a melting point of 125°–127°; $\alpha_D^{25} = -14.8°$ (c=4.94%, methanol) is obtained.

By suitable hydrolysis of the ester of Example 1 in customary manner, for example by reaction in an acidic medium, the following acid is obtained:

(a) 1-{4-[N-(2-isopropoxyethyl)-N-([2R]-2-carboxy-2-aminoethylmercapto-acetyl)-amino]-benzoyl}-4-[2-(4-chlorophenyl)-ethyl]-piperazine.

If, instead of the L-cysteine methyl ester, a corresponding different L-cysteine ester is reacted in accordance with the process of Example !, the following esters are obtained:

(b) 1-{4-[N-(2-isopropoxyethyl)-N-([2R]-2-ethoxycarbonyl-2-aminoethylmercaptoacetyl)-amino]-benzoyl}-4-[2-(4-chlorophenyl)-ethyl]-piperazine. The dihydrochloride monohydrate thereof has a melting point of 123°–126° and an $\alpha_D^{25} = -16.5°$ (c=0.606%, methanol).

(c) 1-{4-[N-(2-isopropoxyethyl)-N-([2R]-2-n-propoxycarbonyl-2-aminoethylmercaptoacetyl)-amino]-benzoyl}-4-[2-(4-chlorophenyl)-ethyl]-piperazine (d) 1-{4-[N-(2-isopropoxyethyl)-N-([2R]-2-isopropoxycarbonyl-2-aminoethylmercaptoacetyl)-amino]-benzoyl}-4-[2-(4-chlorophenyl)-ethyl]-piperazine (e) 1-{4-[N-(2-isopropoxyethyl)-N-([2R]-2-n-butoxycarbonyl-2-aminoethylmercaptoacetyl)-amino]-benzoyl}-4-[2-(4-chlorophenyl)-ethyl]-piperazine (f) 1-{4-[N-(2-isopropoxyethyl)-N-([2R]-2-sec-butoxycarbonyl-2-aminoethylmercaptoacetyl)-amino]-benzoyl}-4-[2-(4-chlorophenyl)-ethyl]-piperazine (g) 1-{4-[N-(2-isopropoxyethyl)-N-([2R]-2-isobutoxycarbonyl-2-aminoethylmercaptoacetyl)-amino]-benzoyl}-4-[2-(4-chlorophenyl)-ethyl]-piperazine (h) 1-{4-[N-(2-isopropoxyethyl)-N-([2R]-2-tert-butoxycarbonyl-2-aminoethylmercaptoacetyl)-amino]-benzoyl}-4-[2-(4-chlorophenyl)-ethyl]-piperazine.

The esters 1(b) to 1(h) can also be obtained by esterification of the acid of Example 1(a) in a suitable manner, for example by reaction with the corresponding alkanol.

EXAMPLE 2

Analogously to Example 1, 1-{4-[N-(2-isopropoxyethyl)-N-chloroacetylamino]-benzoyl}-4-[2-(4-chlorophenyl)-ethyl]-piperazine hydrochloride is reacted with N-acetyl-3-mercapto-D-valine (=N-acetyl-D-penicillamine), yielding 1-{4-[N-(2-isopropoxyethyl)-N-([2R]-2-carboxy-2-N'-acetylamino-1,1-dimethyl-ethylmercapto-acetyl)-amino]-benzoyl}-4-[2-(4-chlorophenyl)-ethyl]-piperazine.

If, instead of N-acetyl-3-mercapto-D-valine, a corresponding alkyl ester is reacted in accordance with the process of Example 2, the following esters are obtained:
  (a) 1-{4-[N-(2-isopropoxyethyl)-N-([2R]-2-methoxycarbonyl-2-N'-acetylamino-1,1-dimethyl-ethylmercapto-acetyl)-amino]-benzoyl}-4-[2-(4-chlorophenyl)-ethyl]-piperazine
  (b) 1-{4-[N-(2-isopropoxyethyl)-N-([2R]-2-ethoxycarbonyl-2-N'-acetylamino-1,1-dimethyl-ethylmercapto-acetyl)-amino]-benzoyl}-4-[2-(4-chlorophenyl)-ethyl]-piperazine.

The esters 2(a) and 2(b) can also be obtained by esterification of the acid of Example 2 in a suitable manner, for example by reaction with the corresponding alkanol.

EXAMPLE 3

Analogously to Example 1, 1-{4-[N-(2-isopropoxyethyl)-N-chloroacetylamino]-benzoyl}-4-[2-(4-chlorophenyl)-ethyl]-piperazine hydrochloride is reacted with 3-mercapto-DL-valine (=DL-penicillamine), yielding (±)-1-{4-[N-(2-isopropoxyethyl)-N-(2-carboxy-2-amino-1,1-dimethyl-ethylmercapto-acetyl)-amino]-benzoyl}-4-[2-(4-chlorophenyl)-ethyl]-piperazine.

If, instead of 3-mercapto-DL-valine, a corresponding alkyl ester is reacted in accordance with the process of Example 3, the following esters are obtained:
  (a) (±)-1-{4-[N-(2-isopropoxyethyl)-N-(2-methoxycarbonyl-2-amino-1,1-dimethyl-ethylmercapto-acetyl)-benzoyl}-4-[2-(4-chlorophenyl)-ethyl]-piperazine
  (b) (±)-1-{4-[N-(2-isopropoxyethyl)-N-(2-ethoxycarbonyl-2-amino-1,1-dimethyl-ethylmercapto-acetyl)-benzoyl}-4-[2-(4-chlorophenyl)-ethyl]-piperazine.

The esters 3(a) and 3(b) can also be obtained by esterification of the acid of Example 3 in a suitable manner, for example by reaction with the corresponding alkanol.

EXAMPLE 4

Analogously to Example 1, 1-{4-[N-(2-isopropoxyethyl)-N-chloroacetylamino]-benzoyl}-4-[2-(4-chlorophenyl)-ethyl]-piperazine hydrochloride is reacted with DL-2-mercapto-succinic acid (=DL-thiomalic acid), yielding (±)-1-{4-[N-(2-isopropoxyethyl)-N-(1,2-dicarboxyethylmercapto-acetyl)-amino]-benzoyl}-4-[2-(4-chlorophenyl)-ethyl]-piperazine.

If instead of DL-2-mercapto-succinic acid, a corresponding dialkyl ester is reacted in accordance with the process of Example 4, the following esters are obtained:
  (a) (±)-1-{4-[N-(2-isopropoxyethyl)-N-(1,2-dimethoxycarbonyl-ethylmercapto-acetyl)-amino]-benzoyl}-4-[2-(4-chlorophenyl)-ethyl]-piperazine
  (b) (±)-1-{4-[N-(2-isopropoxyethyl)-N-( 1,2-diethoxycarbonyl-ethylmercapto-acetyl)-amino]-benzoyl}-4-[2-(4-chlorophenyl)-ethyl]-piperazine.

The esters 4(a) and 4(b) can also be obtained by esterification of the dicarboxylic acid of Example 4 in a suitable manner, for example by reaction with the corresponding alkanol.

EXAMPLE 5

Analogously to Example 1, 2.0 g of 1-{4-[N-(2-isopropoxyethyl)-N-chloroacetyl-amino]-benzoyl}-4-[2-(4-chlorophenyl)-ethyl]-piperazine—freed from the corresponding hydrochloride by treatment with a mixture of aqueous ammonia solution/methylene chloride—are reacted with 0.571 g of N-acetyl-L-cysteine, yielding 1-{4-[N-(2-isopropoxyethyl)-N-([2R]-2-carboxy-2-N'-acetylamino-ethylmercapto-acetyl)-amino]-benzoyl}-4-[2-(4-chlorophenyl)-ethyl]-piperazine. The hydrochloride hexhydrate thereof has a melting point of 132°–135° and an $\alpha_D{}^{25} = -12.5°$ (c=1.095%, methanol).

If, instead of N-acetyl-L-cysteine, a corresponding alkyl ester is reacted in accordance with the process of Example 5, the following esters are obtained:
  (a) 1-{4-1N-(2-isopropoxyethyl)-N-([2R]-2-methoxycarbonyl-2-N'-acetylamino-ethylmercapto-acetyl)-amino]-benzoyl}-4-[2-(4-chlorophenyl)-ethyl]-piperazine
  (b) 1-{4-[N-(2-isopropoxyethyl)-N-([2R]-2-ethoxycarbonyl-2-N'-acetylamino-ethylmercapto-acetyl)-amino]-benzoyl}-4-[2-(4-chlorophenyl)-ethyl]-piperazine
  (c) 1-{4-[N-(2-isopropoxyethyl)-N-([2R]-2-n-propoxycarbonyl-2-N'-acetylamino-ethylmercapto-acetyl)-amino]-benzoyl}-4-[2-(4-chlorophenyl)-ethyl]-piperazine
  (d) 1-{4-[N-(2-isopropoxyethyl)-N-([2R]-2-isopropoxycarbonyl-2-N'-acetylamino-ethylmercapto-acetyl)-amino]-benzoyl}-4-[2-(4-chlorophenyl)-ethyl]-piperazine
  (e) 1-{4-[N-(2-isopropoxyethyl)-N-([2R]-2-n-butoxycarbonyl-2-N'-acetylamino-ethylmercapto-acetyl)-amino]-benzoyl}-4-[2-(4-chlorophenyl)-ethyl]-piperazine
  (f) 1-{4-[N-(2-isopropoxyethyl)-N-([2R]-2-sec-butoxycarbonyl-2-N'-acetylamino-ethylmercapto-acetyl)-amino]-benzoyl}-4-[2-(4-chlorophenyl)-ethyl]-piperazine
  (g) 1-{4-[N-(2-isopropoxyethyl)-N-([2R]-2-isobutoxycarbonyl-2-N'-acetylamino-ethylmercapto-acetyl)-amino]-benzoyl}-4-[2-(4-chlorophenyl)-ethyl]-piperazine
  (h) 1-{4-[N-(2-isopropoxyethyl)-N-([2R]-2-tert-butoxycarbonyl-2-N'-acetylamino-ethylmercapto-acetyl)-amino]-benzoyl}-4-[2-(4-chlorophenyl)-ethyl]-piperazine.

The esters 5(a) to 5(h) can also be obtained by esterification of the acid of Example 5 in a suitable manner, for example by reaction with the corresponding alkanol.

EXAMPLE 6

Analogously to Example 1, 1.0 g of 1-{4-[N-(2-isopropoxyethyl)-N-chloroacetyl-amino]-benzoyl}-4-[2-(4-chlorophenyl)-ethyl]-piperazine—freed from the corresponding hydrochloride by treatment with a mixture of aqueous ammonia solution/methylene chloride—is reacted with 0.24 g of 3-mercapto-propionic acid methyl ester, yielding 1-{4-[N-(2-isopropoxyethyl)-N-(2-methoxycarbonyl-ethylmercapto-acetyl)-amino]-benzoyl}-4-[2-(4-chlorophenyl)-ethyl]-piperazine. The hydrochloride monohydrate thereof has a melting point of 91°–94°.

By suitable hydrolysis of the ester of Example 6 in customary manner, for example by reaction in an acidic medium, the following acid is obtained:
  (a) 1-{4-[N-(2-isopropoxyethyl)-N-(2-carboxy-ethylmercapto-acetyl)-amino]-benzoyl}-4-[2-(4-chlorophenyl)-ethyl]-piperazine.

EXAMPLE 7

Analogously to Example 1, 1-{4-[N-(2-isopropoxyethyl)-N-chloroacetylamino]-benzoyl}-4-[2-(4-chlorophenyl)-ethyl]-piperazine hydrochloride is reacted with 3-mercapto-2-oxopropionic acid (=mercaptopyruvic acid), yielding 1-{4-[N-(2-isopropoxyethyl)-N-(2-carboxy-2-oxo-ethylmercapto-acetyl)-amino]-benzoyl}-4-[2-(4-chlorophenyl)-ethyl]-piperazine.

If, instead of 3-mercapto-2-oxopropionic acid, a corresponding alkyl ester is reacted in accordance with the process of Example 7, the following esters are obtained:
  (a) 1-{4-[N-(2-isopropoxyethyl)-N-(2-methoxycarbonyl-2-oxo-ethylmercapto-acetyl)-amino]-benzoyl}-4-[2-(4-chlorophenyl)-ethyl]-piperazine
  (b) 1-{4-[N-(2-isopropoxyethyl )-N-(2-ethoxycarbonyl-2-oxo-ethylmercapto-acetyl)-amino]-benzoyl}-4-[2-(4-chlorophenyl)-ethyl]-piperazine.

The esters 7(a) and 7(b) can also be obtained by esterification of the acid of Example 7 in suitable manner, for example by reaction with the corresponding alkanol.

EXAMPLE 8

1 g of 1-{4-[N-(2-isopropoxyethyl)-N-chloroacetylamino]-benzoyl}-4-[2-(4-chlorophenyl-ethyl]-piperazine hydrochloride, m.p. 146°–147°, is suspended in 40 ml of water. 20 ml or ether are then added, the hydrochloride being almost completely dissolved. 0.4 g of L-glutathione (reduced form, supplied by Fluka) [=γ-L-glutamyl-L-cysteinyl-glycine] is added. Then 1 ml of concentrated aqueous ammonia solution is added. A milky emulsion having a pit of about 12 is formed. Clear layers form within a short period of time. Alter being stirred vigorously for 14 hours under a continuous current of $N_2$, the two-phase reaction mixture is diluted with ether; the organic phase is separated off and washed with water, dried and concentrated by evaporation. The glassy material is stirred with 10 ml of methanol and the resulting solution is diluted with 150 ml of acetone. A lumpy material is precipitated. After decanting, 30 ml of acetone are added to the material and the mixture is stirred with heating, yielding a crystalline material which is filtered off with suction. This material corresponds to 1-{{4-{N-(2-isopropoxyethyl)-N-[[[2R]-2-[N'-(carboxymethyl)carbamoyl]-2-[N''-(γ-L-glutamyl)amino]-ethylmercapto-acetyl]]-amino}-benzoyl}}-4-[2-(4-chlorophenyl)-ethyl]-piperazine having a melting point of 126°–129°. When the substance is dried, dissolved in methanol and reprecipitated by the addition of ether, a product having a melting point of 168°–173° is obtained.

EXAMPLE 9

Analogously to Example 1, 1-{4-[N-(2-isopropoxyethyl)-N-chloroacetylamino]-benzoyl}-4-[2-(4-chlorophenyl)-ethyl]-piperazine hydrochloride is reacted with DL-homocysteine (=2-amino-4-mercaptobutyric acid), yielding (±)-1-{4-[N-(2-isopropoxyethyl)-N-(3carboxy-3-amino-propylmercapto-acetyl)-amino]-benzoyl}-4-[2-(4-chlorophenyl)-ethyl]-piperazine.

If, instead of DL-homocysteine, a corresponding alkyl ester is reacted in accordance with the process of Example 9, the following esters are obtained:
  (a) (±)-1-{4-[N-(2-isopropoxyethyl)-N-(3-methoxycarbonyl-3-amino-propylmercaptoacetyl)-amino]-benzoyl}-4-[2-(4-chlorophenyl)-ethyl]-piperazine
  (b) (±)-1-{4-[N-(2-isopropoxyethyl)-N-(3-ethoxycarbonyl-3-amino-propylmercaptoacetyl)-amino]-benzoyl}-4-[2-(4-chlorophenyl)-ethyl]-piperazine.

The esters 9(a) and 9(b) can also be obtained by esterification of the acid of Example 9 in a suitable manner, for example by reaction with the corresponding alkanol.

EXAMPLE 10

Analogously to Example 1, 1.6 g of 1-{4-[N-(2-isopropoxyethyl)-N-chloroacetyl-amino]-benzoyl}-4-[2-(4-chlorophenyl)-ethyl]-piperazine—freed from the corresponding hydrochloride by treatment with a mixture of aqueous ammonia solution/methylene chloride—are reacted with 0.55 g of L-cysteinyl-glycine, yielding 1-{{4-{N-2-isopropoxyethyl)-N-[[[2R]-2-[N'-(carboxymethyl)carbamoyl]-2-amino-ethylmercaptoacetyl]]-amino}-benzoyl}}-4-[2-(4-chlorophenyl)-ethyl]-piperazine. The hemihydrate thereof has a melting point of 85°–87° and an $a_D{}^{25} = -1.5°$ (c=0.545%, methanol).

EXAMPLE 10a

Analogously to Example 1, 1-{4-[N-(2-isopropoxyethyl)-N-chloroacetylamino]-benzoyl}-4-[2-(4-chlorophenyl)-ethyl]-piperazine hydrochloride is reacted with γ-L-glutamyl-L-cysteine, yielding 1-{{4-{N-(2-isopropoxyethyl)-N-[[[2R]-2-carboxy-2-[N'-(γ-L-glutamyl)amino]-ethylmercapto-acetyl]]-amino}-benzoyl}}-4-[2-(4-chlorophenyl)-ethyl]-piperazine.

EXAMPLE 11

Analogously to Example 1, 1-{4-1N-(2-isopropoxyethyl)-N-chloroacetylamino]-benzoyl}-4-[2-(4-chlorophenyl)-ethyl]-piperazine hydrochloride is reacted with D-cysteine methyl ester, yielding (+)-1-{4-[N-(2-isopropoxyethyl)-N-([2S]-2-methoxycarbonyl-2-aminoethylmercapto-acetyl)-amino]-benzoyl}-4-[2-(4-chlorophenyl)-ethyl]-piperazine.

EXAMPLE 12

Analogously to Example 1, 2.0 g of 1-{4-[N-(2-isopropoxyethyl)-N-chloroacetyl-amino]-benzoyl}-4-[2-(4-chlorophenyl)-ethyl]-piperazine—freed from the corresponding hydrochloride by treatment with a mixture of aqueous ammonia solution/methylene chloride—are reacted with 1.29 g of N-acetyl-L-glutathione (reduced form) [=γ-N-acetyl-L-glutamyl-L-cysteinyl-glycine], yielding 1-{{4-{N-(2-isopropoxyethyl)--N-[[[2R]-2-[N'-(carboxymethyl)carbamoyl]-2-[N''-(γ-N'''-acetyl-L-glutamyl)amino]-ethylmercapto-acetyl]]-amino}-benzoyl}}-4-[2-(4-chlorophenyl)-ethyl]-piperazine. The trihydrate thereof has a melting point of 149°–152° and an $a_D{}^{25} = -23.5°$ (c=0.4986%, methanol).

EXAMPLE 13

Analogously to Example 1, 1-{4-[N-(2-isopropoxyethyl)-N-chloroacetylamino]-benzoyl}-4-[2-(4-chlorophenyl)-ethyl]-piperazine hydrochloride is reacted with 2-mercaptoacetic acid methyl ester, yielding 1-{4-[N-(2- isopropoxyethyl)-N-(methoxycarbonyl-methylmercapto-acetyl)-amino]-benzoyl}-4-[2-(4-chlorophenyl)-ethyl]-piperazine.

EXAMPLE 14

Analogously to Example 1, 1-{4-[N-(2-isopropoxyethyl)-N-chloroacetylamino]-benzoyl}-4-[2-(4-chlorophenyl)-ethyl]-piperazine hydrochloride is reacted with 4-mercaptobutyric acid, yielding 1-{4-[N-(2-isopropoxyethyl)-N-(3-carboxy-propylmercapto-acetyl)-amino]-benzoyl}-4-[2-(4-chlorophenyl)-ethyl]-piperazine.

EXAMPLE 15

Analogously to Example 1, 1-{4-[N-(2-isopropoxyethyl)-N-chloroacetylamino]-benzoyl}-4-[2-(4-chlorophenyl)-ethyl]-piperazine hydrochloride is reacted with cysteamine (=2-mercaptoethylamine), yielding 1-{4-[N-(2-isopropoxyethyl)-N-(2-aminoethylmercapto-acetyl)-amino]-benzoyl}-4-[2-(4-chlorophenyl)-ethyl]-piperazine.

EXAMPLE 16

If, in Examples 1 to 15, instead of the optically active starting materials in the L-form, there are used the D-forms or racemates thereof, there are obtained the corresponding enantiomers or racemates of the end products obtained in those Examples.

EXAMPLE 17

If, in Examples 1 to 15, instead of the optically active starting materials in the D-form, there are used the L-forms or racemates thereof, there are obtained the corresponding enantiomers or racemates of the end products obtained in those Examples.

EXAMPLE 18

If, in Examples 1 to 15, instead of the racemic starting materials, there are used the L-forms or D-forms thereof, there are obtained the corresponding optical antipodes of the end products obtained in those Examples.

EXAMPLE 19

If, in Examples 1 to 18, 1-{4-[N-(2-hydroxyethyl)-N-chloroacetyl-amino]-benzoyl}-4-[2-(4-chlorophenyl)-ethyl]-piperazine is used as starting material instead of 1-{4-[N-(2-isopropoxyethyl)-N-chloroacetyl-amino]-benzoyl}-4-[2-(4-chlorophenyl)-ethyl]-piperazine hydrochloride, the following compounds are obtained in analogous manner:

(a) 1-{4-[N-(2-hydroxyethyl)-N-([2R]-2-methoxycarbonyl-2-aminoethylmercapto-acetyl)-amino]-benzoyl}-4-[2-(4-chlorophenyl)-ethyl]-piperazine (b) 1-{4-[N-(2-hydroxyethyl)-N-([2R]-2-carboxy-2-aminoethylmercapto-acetyl)-amino]-benzoyl}-4-[2-(4-chlorophenyl)-ethyl]-piperazine (c) 1-{4-[N-(2-hydroxyethyl)-N-([2R ]-2-ethoxycarbonyl-2-aminoethylmercapto-acetyl)-amino]-benzoyl}-4-[2-(4-chlorophenyl)-ethyl]-piperazine (d) 1-{4-[N-(2-hydroxyethyl)-N-([2R]-2-carboxy-2-N'-acetylamino-1,1-dimethyl-ethylmercapto-acetyl)-amino]-benzoyl}-4-[2-(4-chlorophenyl)-ethyl]-piperazine (e) 1-{4-[N-(2-hydroxyethyl)-N-([2R]-2-methoxycarbonyl-2-N'-acetylamino-1,1-dimethyl-ethylmercapto-acetyl)-amino]-benzoyl}-4-[2-(4-chlorophenyl)-ethyl]-piperazine (f) 1-{4-[N-(2-hydroxyethyl)-N-([2R]-2-ethoxycarbonyl-2-N'-acetylamino-1,1-dimethylethylmercapto-acetyl)-amino]-benzoyl}-4-[2-(4-chlorophenyl)-ethyl]-piperazine (g) (±)-1-{4-[N-(2-hydroxyethyl)-N-(2-carboxy-2-amino-1,1-dimethyl-ethylmercapto-acetyl)-amino]-benzoyl}-4-[2-(4-chlorophenyl)-ethyl]-piperazine (h) (±)-1-{4-[N-(2-hydroxyethyl)-N-(2-methoxycarbonyl-2-amino-1,1-dimethyl-ethylmercapto-acetyl-amino]-benzoyl}-4-[2-(4-chlorophenyl)-ethyl]-piperazine (i) (±)-1-{4-[N-(2-hydroxyethyl)-N-(2-ethoxycarbonyl-2-amino-1,1-dimethyl-ethylmercapto-acetyl)-amino]-benzoyl}-4-[2-(4-chlorophenyl)-ethyl]-piperazine (j) (±)-1-{4-[N-(2-hydroxyethyl)-N-(1,2-dicarboxyethylmercapto-acetyl)-amino]-benzoyl}-4-[2-(4-chlorophenyl)-ethyl]-piperazine (k) (±)-1-{4-[N-(2-hydroxyethyl)-N-(1,2-di-methoxycarbonyl-ethylmercapto-acetyl)-amino]-benzoyl}-4-[2-(4-chlorophenyl)-ethyl]-piperazine (l) (±)-1-{4-[N-(2-hydroxyethyl)-N-(1,2-di-ethoxycarbonyl-ethylmercapto-acetyl)-amino]-benzoyl}-4-[2-(4-chlorophenyl)-ethyl]-piperazine (m) 1-{4-[N-(2-hydroxyethyl)-N-([2R]-2-carboxy-2-N'-acetylamino-ethylmercapto-acetyl)-amino]-benzoyl}-4-[2-(4-chlorophenyl)-ethyl]-piperazine (n) 1-{4-[N-(2-hydroxyethyl)-N-([2R]-2-methoxycarbonyl-2-N'-acetylamino-ethylmercapto-acetyl)-amino]-benzoyl}-4-[2-(4-chlorophenyl)-ethyl]-piperazine (o) 1-{4-[N-(2-hydroxyethyl)-N-([2R]-2-ethoxycarbonyl-2-N'-acetylamino-ethylmercapto-acetyl)-amino]-benzoyl}-4-[2-(4-chlorophenyl)-ethyl]-piperazine (p) 1-{4-[N-(2-hydroxyethyl)-N-(2-methoxycarbonyl-ethylmercapto-acetyl)-amino]-benzoyl}-4-[2-(4-chlorophenyl)-ethyl]-piperazine (q) 1-{4-[N-(2-hydroxyethyl)-N-(2-carboxy-ethylmercapto-acetyl)-amino]-benzoyl}-4-[2-(4-chlorophenyl)-ethyl]-piperazine (r) 1-{4-[N-(2-hydroxyethyl)-N-(2-carboxy-2-oxo-ethylmercapto-acetyl)-amino]-benzoyl}-4-[2-(4-chlorophenyl)-ethyl]-piperazine (s) 1-{4-[N-(2-hydroxyethyl)-N-(2-methoxycarbonyl-2-oxo-ethylmercapto-acetyl)-amino]-benzoyl}-4-[2-(4-chlorophenyl)-ethyl]-piperazine (t) 1-{4-[N-(2-hydroxyethyl)-N-(2-ethoxycarbonyl-2-oxo-ethylmercapto-acetyl)-amino]-benzoyl}-4-[2-(4-chlorophenyl)-ethyl]-piperazine (u) 1-{{4-{N-(2-hydroxyethyl)-N-[[[2R]-2-[N'-(carboxymethyl)carbamoyl]-2-[N''-(γ-L-glutamyl)]amino]-ethylmercapto-acetyl]]-amino}-benzoyl}}-4-[2-(4-chlorophenyl)-ethyl]-piperazine.
The dihydrochloride monohydrate thereof has a melting point of 140°–143° and an $\alpha_D^{25} = -13.3°$ (c=0.768%, methanol).

(v) (±)-1-{4-[N-(2-hydroxyethyl)-N-(3-carboxy-3-amino-propylmercapto-acetyl)-amino]-benzoyl}-4-[2-(4-chlorophenyl)-ethyl]-piperazine (w) (±)-1-{4-[N-(2-hydroxyethyl)-N-(3-methoxycarbonyl-3-amino-propylmercapto-acetyl)-amino]-benzoyl}-4-[2-(4-chlorophenyl)-ethyl]-piperazine (x) (±)-1-{4-[N-(2-hydroxyethyl)-N-(3-ethoxycarbonyl-3-amino-propylmercapto-acetyl)-amino]-benzoyl}-4-[2-(4-chlorophenyl)-ethyl]-piperazine (y) 1-{{4-{N-(2-hydroxyethyl)-N-[[[2R]-2-[N'-(carboxymethyl)carbamoyl]-2-amino-ethylmercaptoacetyl]]-amino}-benzoyl}}-4-[2-(4-chlorophenyl)-ethyl]-piperazine (z) 1-{4-[N-(2-hydroxyethyl)-N-([2S]-2-methoxycarbonyl-2-aminoethylmercapto-acetyl)-amino]-benzoyl}-4-[2-(4-chlorophenyl)-ethyl]-piperazine (aa) 1-{{4-{N-(2-hydroxyethyl)-N-[[[2R]-2-[N'-(carboxymethyl)carbamoyl]-2-[N''-(γ-N'''-acetyl--L-glutamyl)amino]-ethylmercapto-acetyl]]-amino}-benzoyl}}-4-[2-(4-chlorophenyl)ethyl]-piperazine (ab) 1-{4-[N-(2-hydroxyethyl)-N-(methoxycarbonyl-methylmercapto-acetyl)-amino]-benzoyl}-4-[2-(4-chlorophenyl)-ethyl]-piperazine (ac) 1-{4-[N-(2-hydroxyethyl)-N-(3-carboxy-propyl-mercapto-acetyl)-amino]-benzoyl}-4-[2-(4-chlorophenyl)-ethyl]-piperazine (ad) 1-{4-[N-(2-hydroxyethyl)-N-(2-aminoethylmercapto-acetyl)-amino]-benzoyl}-4-[2-(4-chlorophenyl)-ethyl]-piperazine.

The starting material is prepared as follows:

Starting material: 1-{4-[N-(2-hydroxyethyl)-N-chloroacetyl-amino]-benzoyl}-4-[2-(4-chlorophenyl)-ethyl]-piperazine 4.9 g of 1-{4-[N-(2-chloroacetoxy-ethyl)-N-chloroacetyl-amino]-benzoyl}-4-[2-(4-chlorophenyl)-ethyl]-piperazine are dissolved in 30 ml of ethanol; 30 ml of water are added and the mixture is adjusted to pH 9.5 with approximately 2.5 ml of concentrated ammonia. After stirring for 2 hours at room temperature, the ethanol is removed in vacuo and the aqueous solution is extracted by shaking with methylene chloride, dried and concentrated by evaporation. The dark oil is chromatographed over 150 g of silica gel and the eluate obtained with methylene chloride/methanol 100:4 is crystallised from isopropanol/ether. The starting material, m.p. 123°–125°, is obtained.

The starting compound is prepared as follows:

6 g of 1-(4-aminobenzoyl)-4-[2-(4-chlorophenyl)ethyl]-piperazine (see EP-A-489 690, Example 3), 2.4 g of 2-bromoethanol and 0.6 g of 4-dimethylaminopyridine are suspended in 80 ml of isopropanol and boiled at reflux for 22 hours, then concentrated by evaporation and partitioned between methylene chloride and 1N sodium hydroxide solution. The organic phase is washed with water, dried and concentrated by evaporation. The oily material is chromatographed over 150 g of silica gel. Elution with methylene chloride/methanol (100:4 and 100:5) yields 1-[4-N-(2-hydroxyethyl)-amino]-benzoyl]-4-[2-(4-chlorophenyl)-ethyl]-piperazine, m.p. 94°–95°.

3.4 g of 1-[4-N-(2-hydroxyethyl)-amino]-benzoyl]-4-[2-(4-chlorophenyl)-ethyl]-piperazine are dissolved in 80 ml of methylene chloride and placed in a container together with 2.4 g of Hünig base (=N-ethyldiisopropylamine). A solution of 2.1 g of chloroacetyl chloride in 15 ml of methylene chloride are added dropwise thereto in the course of 30 minutes. After being stirred for 3.5 hours at room temperature, the dark solution is washed neutral with water, dried and concentrated by evaporation, yielding oily 1-{4-[N-(2-chloroacetoxy-ethyl)-N-chloroacetyl-amino]-benzoyl}-4-[2-(4-chlorophenyl)-ethyl]-piperazine, which is reacted further without purification.

The starting material, 1-{4-[N-(2-hydroxyethyl)-N-chloroacetyl-amino]-benzoyl}-4-[2-(4-chlorophenyl)-ethyl]-piperazine, like the compounds of formula I, acts as an inhibitor on the biosynthesis of interleukin-1 and can be used in the same manner as the compounds of formula I in the treatment of the above-mentioned disorders. The invention therefore relates also to that compound, including the salts thereof, to pharmaceutical compositions comprising that compound and to its use and preparation.

EXAMPLE 20

If, in Examples 1 to 18, 1-(4-N-chloroacetylaminobenzoyl)-4-[2-(4-chlorophenyl)-ethyl]-piperazine is used as starting material instead of 1-{4-[N-(2-isopropoxyethyl)-N-chloroacetyl-amino]-benzoyl}-4-[2-(4-chlorophenyl)-ethyl]-piperazine hydrochloride, the following compounds are obtained in analogous manner:

(a) 1-{4-[N-([2R]-2-methoxycarbonyl-2-aminoethylmercapto-acetyl)-amino]-benzoyl}-4-[2-(4-chlorophenyl)-ethyl]-piperazine (b) 1-{4-[N-([2R]-2-carboxy-2-aminoethylmercapto-acetyl)-amino]-benzoyl}-4-[2-(4-chlorophenyl)-ethyl]-piperazine (c) 1-{4-[N-([2R]-2-ethoxycarbonyl-2-aminoethylmercapto-acetyl)-amino]-benzoyl}-4-[2-(4-chlorophenyl)-ethyl]-piperazine (d) 1-{4-[N-([2R]-2-carboxy-2-N'-acetylamino-1,1-dimethyl-ethylmercapto-acetyl)-amino]-benzoyl}-4-[2-(4-chlorophenyl)-ethyl]-piperazine (e) 1-{4-[N-([2R]-2-methoxycarbonyl-2-N'-acetylamino-1,1-dimethyl-ethylmercapto-acetyl)-amino]-benzoyl}-4-[2-(4-chlorophenyl)-ethyl]-piperazine (f) 1-{4-[N-([2R]-2-ethoxycarbonyl-2-N'-acetylamino-1,1-dimethyl-ethylmercapto-acetyl)-amino]-benzoyl}-4-[2-(4-chlorophenyl)-ethyl]-piperazine (g) (±)-1-{4-[N-(2-carboxy-2-amino-1,1-dimethyl-ethylmercapto-acetyl)-amino]-benzoyl}-4-[2-(4-chlorophenyl)-ethyl]-piperazine (h) (±)-1-{4-[N-(2-methoxycarbonyl-2-amino-1,1-dimethyl-ethylmercapto-acetyl)-amino]-benzoyl}-4-[2-(4-chlorophenyl)-ethyl]-piperazine (i) (±)-1-{4-[N-(2-ethoxycarbonyl-2-amino-1,1-dimethyl-ethylmercapto-acetyl)-amino]-benzoyl}-4-[2-(4-chlorophenyl)-ethyl]-piperazine (j) (±)-1-{4-[N-(1,2-dicarboxyethylmercapto-acetyl)-amino]-benzoyl}-4-[2-(4-chlorophenyl)-ethyl]-piperazine (k) (±)-1-{4-[N-(1,2-di-methoxycarbonyl-ethylmercapto-acetyl)-amino]-benzoyl}-4-[2-(4-chlorophenyl)-ethyl]-piperazine (l) (±)-1-{4-[N-(1,2-di-ethoxycarbonyl-ethylmercapto-acetyl)-amino]-benzoyl}-4-[2-(4chlorophenyl)-ethyl]-piperazine (m) 1-{4-[N-([2R]-2-carboxy-2-N'-acetylamino-ethylmercapto-acetyl)-amino]-benzoyl}-4-[2-(4-chlorophenyl)-ethyl]-piperazine (n) 1-{4-[N-([2R]-2-methoxycarbonyl-2-N'-acetylamino-ethylmercapto-acetyl)-amino]-benzoyl}-4-[2-(4-chlorophenyl)-ethyl]-piperazine (o) 1-{4-[N-([2R]-2-ethoxycarbonyl-2-N'-acetylamino-ethylmercapto-acetyl)-amino]-benzoyl}-4-[2-(4-chlorophenyl)-ethyl]-piperazine (p) 1-{4-[N-(2-methoxycarbonyl-ethylmercapto-acetyl)-amino]-benzoyl}-4-[2-(4-chlorophenyl)-ethyl]-piperazine (q) 1-{4-[N-(2-carboxy-ethylmercapto-acetyl)-amino]-benzoyl}-4-[2-(4-chlorophenyl)-ethyl]-piperazine (r) 1-{4-[N-(2-carboxy-2-oxo-ethylmercapto-acetyl)-amino]-benzoyl}-4-[2-(4-chlorophenyl)-ethyl]-piperazine (s) 1-{4-[N-(2-methoxycarbonyl-2-oxo-ethylmercapto-acetyl)-amino]-benzoyl}-4-[2-(4-chlorophenyl)-ethyl]-piperazine (t) 1- {4-[N-(2-ethoxycarbonyl-2-oxo-ethylmercapto-acetyl)-amino]-benzoyl}-4-[2-(4-chlorophenyl)-ethyl]-piperazine (u) 1-{{4-{N-[[[2R]-2-[N'-(carboxymethyl)carbamoyl]-2-[N''-(γ-L-glutamyl)amino]-ethylmercapto-acetyl]]-amino}-benzoyl}}-4-[2-(4-chlorophenyl)-ethyl]-piperazine (v) (±)-1-{4-[N-(3-carboxy-3-amino-propylmercapto-acetyl)-amino]-benzoyl}-4-[2-(4-chlorophenyl)-ethyl]-piperazine (w) (±)-1-{4-[N-(3-methoxycarbonyl-3-amino-propylmercapto-acetyl)-amino]-benzoyl}-4-[2-(4-chlorophenyl)-ethyl]-piperazine (x) (±)-1-{4-[N-(3-ethoxycarbonyl-3-amino-propyl-mercapto-acetyl)-amino]-benzoyl}-4-[2-(4-chlorophenyl)-ethyl]-piperazine (y) 1-{{4-{N-[[[2R]-2-[N'-(carboxymethyl)carbamoyl]-2-amino-ethylmercapto-acetyl]]-amino}-benzoyl}}-4-[2-(4-chlorophenyl)-ethyl]-piperazine (z) 1-{4-[N-([2S]-2-methoxycarbonyl-2-aminoethyl-mercapto-acetyl)-amino]-benzoyl}-4-[2-(4-chlorophenyl)-ethyl]-piperazine (aa) 1-{{4-{N-[[[2R]-2-[N'-(carboxymethyl)carbamoyl]-2-[N''-(γ-N'''-acetyl-L-glutamyl)amino]-ethylmercapto-acetyl]]-amino}-benzoyl}}-4-[2-(4-chlorophenyl)-ethyl]-piperazine (ab) 1-{4-[N-(methoxycarbonyl-methylmercapto-acetyl)-amino]-benzoyl}-4-[2-(4-chlorophenyl)-ethyl]-piperazine (ac) 1-{4-[N-(3-carboxy-propylmercapto-acetyl)-amino]-benzoyl}-4-[2-(4-chlorophenyl)-ethyl]-piperazine (ad) 1-{4-[N-(2-aminoethylmercapto-acetyl)-amino]-benzoyl}-4-[2-(4-chlorophenyl)-ethyl]-piperazine.

The starting material, 1-( 4-N-chloroacetylaminobenzoyl)-4-[2-(4-chlorophenyl)-ethyl]-piperazine, is prepared as follows:

1.7 g of 1-(4-aminobenzoyl)-4-[2-(4-chlorophenyl)-ethyl]-piperazine (see EP-A-489 690, Example 3) and 0.55 g of triethylamine are placed in a container with 25 ml of methylene chloride. A solution of 0.6 g of chloroacetyl chloride is added dropwise thereto. The dark solution is left to stand overnight, diluted with 50 ml of methylene chloride, washed with 1N sodium hydroxide solution, dried over magnesium sulfate and concentrated by evaporation. The resulting crystals are recrystallised from acetone, yielding the starting material. m.p. 146°–147°.

EXAMPLE 21

3.0 g of 1-{4-[N-(2-isopropoxyethyl)-N-chloroacetyl-amino]-benzoyl}-4-[2-(4-chlorophenyl)-ethyl]-piperazine are suspended in 40 ml of water and 30 ml of ether. 0.93 g of L-cysteine hydrochloride hydrate (supplied by Fluka) is added thereto, with stirring; 3 ml of concentrated aqueous ammonia solution are added dropwise thereto in the course of 5 minutes. A milky emulsion is formed which becomes clear within a short period of time. After being stirred vigorously for 1 hour the two-phase reaction mixture is poured into a separating tunnel. The aqueous phase is separated off, washed with ether and concentrated by evaporation in vacuo. The foamy material is dissolved in 20 ml of water and chromatographed on Antec gel-dodecyltrichlorosilane (OPTI-UP $C_{12}$, Antec AG) [eluant: (1) water, to wash out the organic salts, and (2) acetonitrile/water 4:6, to elute the title compound). The combined fractions are concentrated by evaporation in a rotary evaporator. The resulting foam is dissolved in methanol, and ethereal hydrochloric acid is added (pH 2). The mixture is concentrated by evaporation in a rotary evaporator and thoroughly dried. A foam is obtained, which is stirred with ether/hexane, yielding a suspension, which is filtered with suction. The resulting colourless product corresponds to (−)-1-{4-[N-(2-isopropoxyethyl)-N-([2R]-2-carboxy-2-aminoethylmercapto-acetyl)-amino]-benzoyl}-4-[2-(4-chlorophenyl)-ethyl]-piperazine hydrochloride trihydrate, m.p. 140°–143°, $\alpha_D^{25} = -23.0°$ (c=1.01%, methanol).

EXAMPLE 22

The free base is obtained from the product of Example 21 (hydrochloride) as follows:

2.5 g of hydrochloride are dissolved in water and adjusted to pH 14 with concentrated ammonia; the milky solution is concentrated by evaporation in a rotary evaporator and the residue is dissolved in water and applied to 50 g of Antec gel-dodecyltrichlorosilane (OPTI-UP $C_{12}$, Antec AG), washed out with water, and the free base is then eluted with 20% and 40% aqueous acetonitrile; the eluate is concentrated by evaporation and the residue is digested with ether, filtered with suction, washed with ether/hexane and dried. Colourless (−)-1-{4-[N-(2-isopropoxyethyl)-N-([2R]-2-carboxy-2-aminoethyl-mercapto-acetyl)-amino]-benzoyl}-4-[2-(4-chlorophenyl)-ethyl]-piperazine having a melting point of 91°–92°; $\alpha_D^{25} = -25.2$ (c=0.59%, methanol) is obtained.

EXAMPLE 23

3.5 g of 1-{4-[N-(2-isopropoxyethyl)-N-([2R]-2-carboxy-2-N'-acetylamino-ethylmercapto-acetyl)-amino]-benzoyl}-4-[2-(4-chlorophenyl)-ethyl]-piperazine (Example 5) are dissolved in 100 ml of methanol, and 10 ml of concentrated hydrochloric acid in ether are added. The solution is heated at reflux for 2 hours. The ether is removed in a rotary evaporator and the oily residue is dissolved in ethyl acetate and washed with dilute sodium carbonate solution, dried and concentrated by evaporation. Since partial cleavage of the acetyl group has occurred, the oily product is dissolved in 20 ml of ethyl acetate, and 3 ml of acetic anhydride are added. After 2 hours at 80° the mixture is concentrated by evaporation in a rotary evaporator, and the residue is dissolved in 20 ml of dichloromethane and chromatographed on silica gel (eluant: dichlormethane/methanol 98:2). The oily product is convened in methanol with ethereal hydrochloric acid into 1-{4-[N-(2-isopropoxyethyl)-N-([2R]-2-methoxycarbonyl-2-N'-acetylamino-ethylmercapto-acetyl)-amino]-benzoyl}-4-[2-(4-chlorophenyl)-ethyl]-piperazine hydrochloride hemihydrate having a melting point of 54°–56° [$\alpha_D^{25} = -18.4°$ (c=0.537%, methanol)].

EXAMPLE 24

2.1 g of 1-{4-[N-(2-isopropoxyethyl)-N-([2R]-2-ethoxycarbonyl-2-amino-ethylmercapto-acetyl)-amino]-benzoyl}-4-[2-(4-chlorophenyl)-ethyl]-piperazine (Example 1b) are acetylated in 20 ml of glacial acetic acid and 4 ml of acetic anhydride at 70° (1 hour). The mixture is concentrated by evaporation in a rotary evaporator; ethereal hydrochloric acid is added to the residue in methanol and the mixture is again concentrated by evaporation and the residue is stirred with hexane. 1-{4-[N-(2-isopropoxyethyl)-N-([2R]-2-ethoxycarbonyl-2-N'-acetylamino-ethylmercapto-acetyl)-amino]-benzoyl}-4-[2-(4-chlorophenyl)-ethyl]-piperazinehydrochloride monohydrate having a melting point of 44°–46°, $\alpha_D^{25} = -19.1°$ (c=0.618%, methanol) is obtained.

EXAMPLE 25

3 g of 1-{4-[N-(2-isopropoxyethyl)-N-chloroacetyl-amino]-benzoyl}-4-[2-(4-chlorophenyl)-ethyl]-piperazine are suspended in 50 ml of ether and 50 ml of water. 1.69 g of L-glutathione (reduced form, supplied by Fluka) [=γ-L-glutamyl-L-cysteinyl-glycine] are added thereto. 3 ml of concentrated aqueous ammonia solution are then added. A milky emulsion is formed. Clear layers form in the course of 5 minutes. The mixture is stirred vigorously overnight. The ether phase is separated off and the aqueous phase is washed with ether. The combined organic phases are washed with water, dried and concentrated by evaporation. The oily material is dissolved in dichloromethane, adjusted to pH 14 with concentrated ammonia and shaken, dried and concentrated by evaporation. The residue is dissolved in 300 ml of ethyl acetate, dried over magnesium sulfate and concentrated by evaporation. The residue is stirred with ether, filtered with suction and washed with ether. 1-{{4-{N-(2-isopropoxyethyl)-N-[[[2R]-2-[N'-(carboxymethyl)carbamoyl]-2-[N''-(γ-L-glutamyl)amino]-ethylmercapto-acetyl]]-amino}-benzoyl}}-4-[2-(4-chlorophenyl)-ethyl]-piperazine trihydrate having a melting point of 169°–173°, $\alpha_D^{25} = 18.4°$ (c=1.01% methanol) is obtained.

EXAMPLE 26

2 g of 1-{4-[N-(2-isopropoxyethyl)-N-chloroacetyl-amino]-benzoyl}-4-[2-(4-chlorophenyl)-ethyl]-piperazine are suspended in 40 ml of water and 30 ml of ether. 1.3 g of L-glutathione monoethyl ester (supplied by Bachem) and 3 ml of concentrated ammonia are added thereto. The mixture is stirred thoroughly for 2 hours at room temperature, then concentrated by evaporation, and the residue is chromatographed on Antec gel-dodecyltrichlorosilane (OPTI-UP $C_{12}$, Antec AG). Using an increasing proportion of acetonitrile in water there are eluted (a) 1-{{4-{N-(2-isopropoxyethyl)-N-[[[2R]-2-[N'-(carbamoylmethyl)carbamoyl]-2-[N''-(γ-L-glutamyl)amino]-ethylmercapto-acetyl]]-amino}-benzoyl}}-4-[2-(4-chlorophenyl)-ethyl]-piperazine dihydrate [m.p. 120°–122°, $\alpha_D^{25} = -8.3°$ (c=0.577%, methanol)] and (b) 1-{{4-{N-(2-isopropoxyethyl)-N-[[[2R]-2-[N'-(ethoxycarbonylmethyl)carbamoyl]-2-[N''-(γ-L-glutamyl)amino]-ethylmercapto-acetyl]]-amino}-benzoyl}}-4-[2-(4-chlorophenyl)-ethyl]-piperazine dihydrate [m.p. 95°–97°, $\alpha_D^{25} = -20.8°$ (c=0.495%, methanol)].

EXAMPLE 27

If the reaction of Example 26 is carried out in the presence of Hünig base instead of ammonia, amidation can be avoided and exclusively the ethyl ester is obtained [Example 26 (b)].

EXAMPLE 28

1.33 g of 1-{{4-{N-(2-tetrahydropyran-2-yloxyethyl)-N-[[[2R]-2-[N'-carboxymethyl)carbamoyl]-2-[N''-(γ-L-glutamyl)amino]-ethylmercapto-acetyl]]-amino}-benzoyl}}-4-[2-(4-chlorophenyl)-ethyl]-piperazine are stirred thoroughly for 1 hour in 30 ml of methanol and 4 ml of 2N hydrochloric acid. The mixture is adjusted to pH 7 with 2N sodium hydroxide solution and concentrated by evaporation, and the residue is dissolved in 20 ml of water and chromatographed on Antec gel-dodecyltrichlorosilane (OPTI-UP $C_{12}$, Antec AG) (eluant: 10% and 20% aqueous acetonitrile). The eluate is stirred with ether, filtered with suction and washed with ether. 1-{{4-{N-(2-hydroxyethyl)-N-[[[2R]-2-[N'-(carboxymethyl)carbamoyl]-2-[N''-(γ-L-glutamyl)amino]-ethylmercapto-acetyl]]-amino}-benzoyl}}-4-[2-(4-chlorophenyl)-ethyl]-piperazine monohydrate having a melting point of 160°–162°, $\alpha_D^{25} = -16.0°$ (c=0.512%, methanol) is obtained.

The starting material is prepared as follows:

1-(4-Amino-benzoyl)-4-[2-(4-chlorophenyl)-ethyl]-piperazine is dissolved in 150 ml of tetrahydrofuran. 4.51 g of Hünig base and then, dropwise, in the course of 5 minutes 10.91 g of chloroformic acid benzyl ester (50% toluene solution, supplied by Merck) are added thereto. The internal temperature rises to about 28°. After being stirred for 45 minutes the suspension is concentrated by evaporation in a rotary evaporator, and the residue is dissolved in dichloromethane, washed with water, dried and concentrated by evaporation. The residue is dissolved in 30 ml of dichloromethane and then 200 ml of ether are carefully added. The crystals are filtered off with suction and washed with ether. 1-[4-(N-benzyloxycarbonylamino-benzoyl)-4-[2-(4-chlorophenyl)-ethyl]-piperazine having a melting point of 149°–150° is obtained.

8.5 g thereof are dissolved in 80 ml of dimethyl sulfoxide, and 1.34 g of pulverulent KOH are added. The mixture is stirred for 30 minutes at room temperature and then 4.48 g of 2-tetrahydropyran-2-yloxyethyl bromide (DE 1 237 110, Merck) are added and the mixture is maintained at an internal temperature of 60° for 8 hours. A further 0.5 g of pulverulent KOH and 1.0 g of bromide are then added and the reaction mixture is maintained at 60° for a further 3 hours. The suspension is poured onto 500 ml of ice-water, and 300 ml of ethyl acetate are added. The organic phase is separated off, washed with water and sodium carbonate solution, dried and concentrated by evaporation. The oily residue is dissolved in 50 ml of dichloromethane and chromatographed on silica gel (eluant: water/methanol 99:1 and 98:2). The alkylated product, obtained in the form of a foam, is reacted further without further purification.

9.25 g thereof are hydrogenated in methanol with Pd/C 10%. On so doing first the benzyl group is removed and then the carboxylic acid formed intermediately is decarboxylated. The suspension is filtered on a Hyflo filter and the filtrate is concentrated by evaporation. The yellow oil is dissolved in dichloromethane and washed with 1N sodium hydroxide solution, dried and concentrated by evaporation.

7.36 g of the yellow oil are dissolved in 100 ml of tetrahydrofuran, and 2.61 g of Hünig base are added. At an internal temperature of 3°, 2.11 g of chloroacetyl chloride in 10 ml of tetrahydrofuran are added dropwise thereto. The mixture is allowed to rise to room temperature and is stirred for a further 1 hour. The suspension is concentrated by evaporation, and the residue is dissolved in ethyl acetate and washed with water. The ethyl acetate phase is washed again with 15% sodium carbonate solution, dried and concentrated by evaporation. The brown oil is chromatographed on 90 g of silica gel (eluant: $CH_2Cl_2$/methanol 97:3). The resulting oil is dissolved in dichloromethane, and ethereal hydrochloric acid is added (pH 2). The mixture is concentrated by evaporation and the residue is stirred with ether. 1-{4-[N-(2-tetrahydropyran-2-yloxyethyl)-N-chloroacetyl]-amino-benzoyl}-4-[2-(4-chlorophenyl)-ethyl]-piperazine hydrochloride hemihydrate having a melting point of 97°–100° is obtained.

4.8 g thereof are dissolved in 40 ml of ether and 50 ml of water and reacted as described in Example 1 with 2.8 g of L-glutathione and 5 ml of concentrated ammonia to give 1-{{4-{N-(2-tetrahydropyran-2-yloxyethyl)-N-[[[2R]-2-[N'-(carboxymethyl)carbamoyl]-2-[N''-(γ-L-glutamyl)amino]-ethylmercapto-acetyl]]-amino}-benzoyl}}-4-[2-(4-chlorophenyl)-ethyl-piperazine having a melting point of 130°–133°.

EXAMPLE 29

2.52 g of 1-{4-[N-(2-isopropoxyethyl)-N-chloroacetyl-amino]-benzoyl}-4-[2-(4-chlorophenyl)-ethyl]-piperazine and 1.0 g of D-cysteine hydrochloride (instead of L-cysteine hydrochloride hydrate) are reacted analogously to Example 21. After chromatography on Antec gel dodecyltrichlorosilane (OPTI-UP $C_{12}$, Antec AG) [eluant: (1) water, (2) acetonitrile/water 1:9 to 4:61, (+)-1-{4-[N-(2-isopropoxyethyl)-N-([2S]-2-carboxy-2-aminoethylmercapto-acetyl)-amino]-benzoyl}-4-[2-(4-chlorophenyl)-ethyl]piperazine monohydrate, m.p. 90°92°, $\alpha_D^{25} = +29.5°$ (c=0.572%, methanol) is obtained.

EXAMPLE 30

Tablets, each comprising 50 mg of (−)-1-{4-[N-(2-isopropoxyethyl)-N-(2-methoxycarbonyl-2-aminoethylmercapto-acetyl)-amino]-benzoyl}-4-[2-(4-chlorophenyl)-ethyl]-piperazine dihydrochloride trihydrate, are prepared, for example, as follows:

| Composition (10000 tablets) | |
| --- | --- |
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of potato starch, and the mixture is moistened with an ethanolic solution of the gelatin and granulated through a sieve. After drying, the remainder of the potato starch, the magnesium stearate, the talc and the silicon dioxide are mixed in and the mixture is compressed to form tablets each weighing 145.0 mg and comprising 50.0 mg of active ingredient; if desired the tablets may be provided with dividing notches for finer adaptation of the dose.

EXAMPLE 31

Hard gelatin capsules, each comprising 100 mg of active ingredient, for example (−)-1-{4-[N-(2-isopropoxyethyl)-N-(2-methoxycarbonyl-2-aminoethyl-mercapto-acetyl)-amino]-benzoyl}-4-[2-(4-chlorophenyl)-ethyl]-piperazine dihydrochloride trihydrate, are prepared as follows:

| Composition (for 1000 capsules) | |
| --- | --- |
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added through a sieve of 0.2 mm mesh size to the lyophilised active ingredient. The two components are intimately mixed. Then first the lactose is added through a sieve of 0.6 mm mesh size and then the microcrystalline cellulose is added through a sieve of 0.9 mm mesh size. The mixture is then again intimately mixed for 10 minutes. Finally, the magnesium stearate is added through a sieve of 0.8 mm mesh size. After mixing for a further 3 minutes, 390 mg portions of the resulting formulation are introduced into size 0 hard gelatin capsules.

EXAMPLE 32

Film-coated tablets, each comprising 100 mg of active ingredient, for example (−)-1-{4-[N-(2-isopropoxyethyl)-N-(2-methoxycarbonyl-2-aminoethylmercapto-acetyl)-amino]-benzoyl}-4-[2-(4-chlorophenyl)-ethyl]-piperazine dihydrochloride trihydrate, are prepared as follows:

| Composition (for 1000 film-coated tablets) | |
| --- | --- |
| active ingredient | 100.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed together and moistened with a paste prepared from 15 g of corn starch and water (with heating), and granulated. The granules are dried and the remainder of the corn starch, the talc and the calcium stearate are added and mixed with the granules. The mixture is compressed to form tablets (weight: 280 mg) which are then film-coated with a solution of the hydroxypropylmethylcellulose and the shellac in methylene chloride; final weight of the film-coated tablet: 283 mg.

EXAMPLE 33

A 0.2% injection or infusion solution of an active ingredient, for example (−)-1-{4-[N-(2-isopropoxyethyl)-N-(2-methoxycarbonyl-2-aminoethylmercapto-acetyl)-amino]-benzoyl}-4-[2-(4-chlorophenyl)-ethyl]-piperazine dihydrochloride trihydrate, is prepared as follows:

| Composition (for 1000 ampoules) | |
| --- | --- |
| active ingredient | 5.0 g |
| sodium chloride | 22.5 g |
| phosphate buffer pH = 7.4 | 300.0 g |

| -continued |  |
|---|---|
| Composition (for 1000 ampoules) | |
| demineralised water | ad 2500.0 ml |

The active ingredient and the sodium chloride are dissolved in 1000 ml of water and filtered through a microfilter. The buffer solution is added and the mixture is made up to 2500 ml with water. For the preparation of unit dose forms, 1.0 ml or 2.5 ml portions are introduced into glass ampoules which then contain 2.0 mg or 5.0 mg of active ingredient, respectively.

EXAMPLE 34

In a manner analogous to that described in Examples 30 to 33 it is also possible to prepare pharmaceutical compositions each comprising another of the compounds mentioned in Examples 1 to 29.

What is claimed is:

1. A compound of formula I

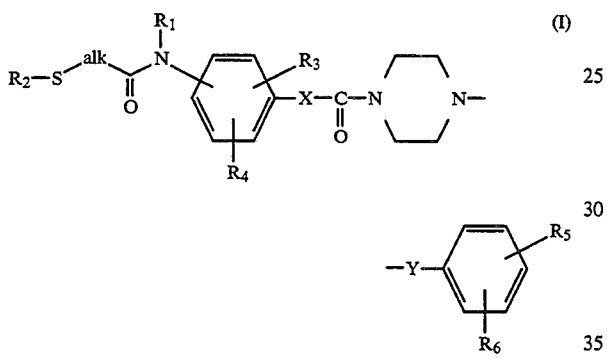

wherein $R_1$ is hydrogen, lower alkyl, hydroxy-lower alkyl, lower alkoxy-lower alkyl, lower alkoxy-lower alkoxy-lower alkyl; phenoxy-lower alkyl or phenyl-lower alkoxy-lower alkyl, the phenyl group in each of the two last-mentioned radicals being unsubstituted or substituted by at least one of lower alkyl, trifluoromethyl, lower alkoxy, halogen and hydroxy; N-lower alkylamino-lower alkyl or N,N-di-lower alkylamino-lower alkyl;

$R_2$ is lower alkyl that is substituted by at least a group (a) substituent and optionally by a group (b) substituent;

said group (a) substituent selected from the group consisting of amino, lower alkanoylamino, carboxy, lower alkoxycarbonyl, carbamoyl, N-lower alkylcarbamoyl, N,N-di-lower alkylcarbamoyl, cyano and a radical —C(=O)—W$_2$; and said group (b) substituent selected from the group consisting of amino, lower alkylamino, di-lower alkylamino, lower alkanoylamino, a radical —NH—W$_1$, oxo, carboxy, lower alkoxycarbonyl, carbamoyl, N-lower alkylcarbamoyl, N,N-di-lower alkylcarbamoyl, cyano, hydroxy, lower alkoxy, lower alkanoyloxy and halogen;

wherein W$_2$ is the residue of a natural amino acid bonded via an amino group, or a lower alkyl ester thereof; and wherein W$_1$ is the residue of a natural amino acid bonded via any carboxy group, or a lower alkyl ester thereof;

$R_3$ and $R_4$ are each independently of the other hydrogen, lower alkyl, halogen, lower alkoxy or lower alkylthio;

$R_5$ and $R_6$ are each independently of the other hydrogen, lower alkyl, halo-lower alkyl, lower alkoxy, lower alkylthio, halogen, amino, lower alkylamino, di-lower alkylamino or lower alkanoylamino;

alk is lower alkylene; and

X and Y are each independently of the other a direct bond, lower alkylene or lower alkenylene;

or a pharmaceutically acceptable salt thereof.

2. A compound of formula I according to claim 1 wherein $R_1$ is hydrogen, lower alkyl, hydroxy-lower alkyl, lower alkoxy-lower alkyl, lower alkoxy-lower alkoxy-lower alkyl, phenoxy-lower alkyl, N-lower alkylamino-lower alkyl or N,N-di-lower alkylamino-lower alkyl;

$R_2$ is lower alkyl that is substituted by at least a group (a) substituent and optionally by a group (b) substituent;

said group (a) substituent selected from the group consisting of amino, carboxy, lower alkoxycarbonyl, carbamoyl, N-lower alkylcarbamoyl, N,N-di-lower alkylcarbamoyl and a radical —C(=O)—W$_2$; and said group (b) substituent selected from the group consisting of amino, lower alkanoylamino, a radical —NH—W$_1$, oxo, carboxy, lower alkoxycarbonyl, carbamoyl, N,N-di-lower alkylcarbamoyl and hydroxy;

wherein W$_2$ is the residue, bonded via an amino group, of a natural amino acid selected from glycine, alanine, valine, leucine and serine, or a lower alkyl ester thereof; and wherein W$_1$ is the residue, bonded via any carboxy group, of a natural amino acid selected from glutamic acid, aspartic acid, glycine, alanine, valine, leucine and serine, or a lower alkyl ester thereof;

$R_3$ and $R_4$ are each independently of the other hydrogen, lower alkyl, halogen, lower alkoxy or lower alkylthio;

$R_5$ and $R_6$ are each independently of the other hydrogen, lower alkyl, trifluoromethyl, lower alkoxy, lower alkylthio, halogen or di-lower alkylamino;

alk is lower alkylene; and

X and Y are each independently of the other a direct bond, lower alkylene or lower alkenylene;

or a pharmaceutically acceptable salt thereof.

3. A compound of formula I according to claim 1 wherein $R_1$ is hydrogen, lower alkyl, hydroxy-lower alkyl or lower alkoxy-lower alkyl;

$R_2$ is lower alkyl that is substituted by at least a group (a) substituent and optionally by a group (b) substituent;

said group (a) substituent selected from the group consisting of amino, carboxy, lower alkoxycarbonyl and a radical —C(=O)—W$_2$;

said group (b) substituent selected from the group consisting of amino, lower alkanoylamino, a radical —NH—W$_1$, oxo, carboxy and lower alkoxycarbonyl;

wherein W$_2$ is the residue, bonded via the amino group, of the amino acid glycine, or a lower alkyl ester thereof; and wherein W₁ is the residue, bonded via the γ-carboxy group, of the amino acid L-glutamic acid, or a lower alkyl ester thereof;

R₃ and R₄ are each independently of the other hydrogen, lower alkyl, halogen, lower alkoxy or lower alkylthio;

R₅ is lower alkylthio, chlorine, fluorine or bromine;

R₆ is hydrogen;

alk is methylene;

X is a direct bond or 1,2-ethenylene; and

Y is 1,2-ethylene;

or a pharmaceutically acceptable salt thereof.

4. A compound according to claim 1 of formula Ia

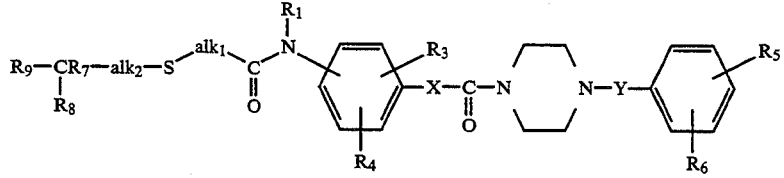

wherein

R₁ is hydrogen, lower alkyl, hydroxy-lower alkyl or lower alkoxy-lower alkyl;

R₃ and R₄ are each independently of the other hydrogen, lower alkyl, chlorine, fluorine, bromine, lower alkoxy or lower alkylthio;

R₅ and R₆ are each independently of the other chlorine, fluorine, bromine, hydrogen, lower alkyl, trifluoromethyl, lower alkoxy or lower alkylthio;

R₇ is hydrogen;

R₈ is hydrogen, amino, lower alkanoylamino or a radical —NH—W₁ wherein W₁ is the residue, bonded via any carboxy group, of a natural amino acid selected from the group consisting of glutamic acid, aspartic acid, glycine, alanine, valine, leucine and serine, or a lower alkyl ester of said W₁ amino acid; or R₇ and R₈ together are oxo;

R₉ is amino, lower alkanoylamino, carboxy, lower alkoxycarbonyl, carbamoyl, N-lower alkylcarbamoyl N,N-di-lower alkylcarbamoyl, cyano or a radical —C(=O)—W₂ wherein W₂ is the residue, bonded via an amino group, of a natural amino acid selected from the group consisting of glycine, alanine, valine, leucine and serine, or a lower alkyl ester of said W₂ amino acid;

alk₁ is lower alkylene;

alk₂ is a direct bond or lower alkylene that is unsubstituted or substituted by carboxy, lower alkoxycarbonyl, carbamoyl, N-lower alkylcarbamoyl, N,N-di-lower alkylcarbamoyl or by cyano;

X is a direct bond or 1,2-ethenylene; and

Y is a direct bond, lower alkylene or 1,2-ethenylene;

or a pharmaceutically acceptable salt thereof.

5. A compound of formula Ia according to claim 4 wherein

R₁ is hydrogen, lower alkyl, hydroxy-lower alkyl or lower alkoxy-lower alkyl;

R₃ and R₄ are each independently of the other hydrogen, lower alkyl, chlorine, fluorine or bromine;

R₅ is chlorine, fluorine, bromine or lower alkylthio;

R₆ is hydrogen;

R₇ is hydrogen;

R₈ is hydrogen, amino, lower alkanoylamino or a radical —NH—W₁ wherein W₁ is the residue, bonded via any carboxy group, of a natural amino acid selected from the group consisting of glutamic acid, aspartic acid, glycine, alanine, valine, leucine and serine, or a lower alkyl ester of said W₁ amino acid;

R₇ and R₈ together are oxo;

R₉ is amino, carboxy, lower alkoxycarbonyl, carbamoyl, N-lower alkylcarbamoyl, N,N-di-lower alkylcarbamoyl or a radical —C(=)—W₂ wherein W₂ is the residue, bonded via an amino group, of a natural amino acid selected from the group consisting of glycine, alanine, valine, leucine and serine, or a lower alkyl ester of said W₂ amino acid;

alk₁ is methylene;

alk₂ is a direct bond, methylene, 1-methyl-methylene, 1,1-dimethyl-methylene, 1-(carboxy or lower alkoxycarbonyl)-methylene or 1,2-ethylene;

X is a direct bond or 1,2-ethenylene; and

Y is 1,2-ethylene;

or a pharmaceutically acceptable salt thereof.

6. A compound of formula Ia according to claim 4 wherein

R₁ is hydrogen, C₁–C₄alkyl, hydroxy-C₂–C₄alkyl or C₁–C₄alkoxy-C₂–C₄alkyl;

R₃ and R₄ are each independently of the other hydrogen, lower alkyl, chlorine, fluorine or bromine;

R₅ is linked in the para-position and is chlorine, fluorine, bromine or lower alkylthio;

R₆ is hydrogen;

R₇ is hydrogen;

R₈ is hydrogen, amino, lower alkanoylamino or a radical —NH—W₁ wherein W₁ is the residue, bonded via any carboxy group, of a natural amino acid selected from glutamic acid, aspartic acid, glycine, alanine, valine, leucine and serine, or a lower alkyl ester of said W₁ amino acid; or R₇ and R₈ together are oxo;

R₉ is amino, carboxy, lower alkoxycarbonyl, carbamoyl, N-lower alkylcarbamoyl, N,N-di-lower alkylcarbamoyl or a radical —C(=O)—W₂ wherein W₂ is the residue, bonded via an amino group, of a natural amino acid selected from glycine, alanine, valine, leucine and serine, or a lower alkyl ester of said W₂ amino acid;

alk₁ is methylene;

alk₂ is a direct bond, methylene, 1,1-dimethyl-methylene, 1-(carboxy or lower alkoxycarbonyl)-methylene or 1,2-ethylene;

X is a direct bond or 1,2-ethenylene; and

Y is 1,2-ethylene;

or a pharmaceutically acceptable salt thereof.

7. A compound of formula Ia according to claim 4 wherein

R₁ is hydrogen, methyl, ethyl, 2-hydroxyethyl or 2-isopropoxyethyl;

R₃ and R₄ are each independently of the other hydrogen, methyl, chlorine or fluorine;

R₅ is linked in the para-position and is chlorine or bromine;

R₆ is hydrogen;

$R_7$ is hydrogen;

$R_8$ is hydrogen, amino, lower alkanoylamino or a radical —NH—$W_1$ wherein $W_1$ is the residue, bonded via the γ-carboxy group, of the amino acid L-glutamic acid, or a lower alkyl ester of said $W_1$ amino acid; or $R_7$ and $R_8$ together are oxo;

$R_9$ is amino, carboxy, lower alkoxycarbonyl or a radical —C(=O)—$W_2$ wherein $W_2$ is the residue, bonded via the amino group, of the amino acid glycine, or a lower alkyl ester of said $W_2$ amino acid;

$alk_1$ is methylene;

$alk_2$ is a direct bond, methylene, 1,1-dimethyl-methylene, 1-(carboxy or lower alkoxycarbonyl)-methylene or 1,2-ethylene;

X is a direct bond or 1,2-ethenylene; and

Y is 1,2-ethylene;

or a pharmaceutically acceptable salt thereof.

8. A compound of formula Ia according to claim 4 wherein $R_8$ is lower alkanoylamino, or a pharmaceutically acceptable salt thereof.

9. (—)-1-{4-[N-(2-isopropoxyethyl)-N-([2R]-2-methoxycarbonyl-2-aminoethylmercapto-acetyl)-amino]-benzoyl}-4-[2-(4-chlorophenyl)-ethyl]-piperazine according to claim 1, or a pharmaceutically acceptable salt thereof.

10. 1-{4-[N-(2-isopropoxyethyl)-N-([2R]-2-carboxy-2-N'-acetylamino-ethylmercapto-acetyl)-amino]-benzoyl}-4-[2-(4-chlorophenyl)ethyl]-piperazine according to claim 1, or a pharmaceutically acceptable salt thereof.

11. A pharmaceutical composition comprising an interleukin-1 inhibitory effective amount of a compound according to claim 1 and at least one pharmaceutically acceptable carrier.

12. A method of treating an interleukin-1 inhibition responsive disease in an animal in need thereof comprising administering to said animal an interleukin-1 inhibiting effective amount of a compound according to claim 1.

* * * * *